(12) United States Patent
Donath et al.

(10) Patent No.: US 8,168,226 B2
(45) Date of Patent: *May 1, 2012

(54) PRODUCTION OF NANOCAPSULES AND MICROCAPSULES BY LAYER-WISE POLYELECTROLYTE SELF-ASSEMBLY

(75) Inventors: Edwin Donath, Giesenhorst (DE); Gleb B. Sukhorukov, Mikroraion (RU); Karl-Heinz Lerche, Berlin (DE); Andreas Voigt, Berlin (DE); Hans Bäumler, Berlin (DE); Frank Caruso, Golm (DE); Helmuth Möhwald, Bingen (DE)

(73) Assignee: Max-Planck-Gesellschaft zur Forderung der Wissenschaften E.V., Munich (DE)

( * ) Notice: Subject to any disclaimer, the term of this patent is extended or adjusted under 35 U.S.C. 154(b) by 1439 days.

This patent is subject to a terminal disclaimer.

(21) Appl. No.: 11/502,180

(22) Filed: Aug. 10, 2006

(65) Prior Publication Data

US 2006/0275373 A1    Dec. 7, 2006

Related U.S. Application Data

(63) Continuation of application No. 10/376,386, filed on Feb. 27, 2003, now Pat. No. 7,101,575, which is a continuation of application No. 09/646,742, filed as application No. PCT/EP99/01855 on Mar. 19, 1999, now abandoned.

(30) Foreign Application Priority Data

| Mar. 19, 1998 | (DE) | 198 12 083 |
| Jul. 15, 1998 | (EP) | 98113181 |
| Feb. 22, 1999 | (DE) | 199 07 552 |

(51) Int. Cl.
| A61K 9/16 | (2006.01) |
| A61K 9/28 | (2006.01) |
| A61K 9/14 | (2006.01) |

(52) U.S. Cl. ............ 424/490; 424/489; 427/2.14
(58) Field of Classification Search .............. None
See application file for complete search history.

(56) References Cited

U.S. PATENT DOCUMENTS

| 3,041,289 | A | 6/1962 | Katchen et al. |
| 3,251,800 | A | 5/1966 | Colley et al. |
| 3,429,827 | A | 2/1969 | Ruus |
| 3,855,172 | A | 12/1974 | Iller et al. |
| 4,001,140 | A | 1/1977 | Foris et al. |
| 4,087,376 | A | 5/1978 | Foris et al. |
| 4,409,331 | A | 10/1983 | Lim |
| 4,487,785 | A | 12/1984 | Goosen et al. |
| 4,495,288 | A | 1/1985 | Jarvis, Jr. et al. |
| 4,663,286 | A | 5/1987 | Tsang et al. |
| 4,683,092 | A | 7/1987 | Tsang |
| 4,741,872 | A | 5/1988 | De Luca |
| 4,835,248 | A | 5/1989 | Bader et al. |
| 4,940,588 | A | 7/1990 | Sparks |
| 5,091,187 | A | 2/1992 | Haynes |
| 5,162,486 | A | 11/1992 | Follmann et al. |
| 5,308,701 | A | 5/1994 | Cohen et al. |
| 5,344,487 | A | 9/1994 | Whalen-Shaw |
| 5,427,767 | A | 6/1995 | Kresse et al. |
| 5,487,390 | A | 1/1996 | Cohen et al. |
| 5,512,332 | A | 4/1996 | Liberti et al. |
| 5,674,519 | A | 10/1997 | Curtis et al. |
| 5,705,222 | A | 1/1998 | Somasundaran et al. |
| 5,716,709 | A | 2/1998 | Ferguson et al. |
| 5,756,210 | A | 5/1998 | Dupuis et al. |
| 6,013,284 | A | 1/2000 | De Miguel et al. |
| 6,017,559 | A | 1/2000 | Mulqueen et al. |
| 6,051,372 | A * | 4/2000 | Bayerl et al. .......... 435/4 |
| 6,203,909 | B1 | 3/2001 | Chassot |
| 6,423,338 | B1 | 7/2002 | Larson et al. |
| 6,479,146 | B1 | 11/2002 | Caruso et al. |
| 6,689,478 | B2 | 2/2004 | Laguitton |
| 6,699,501 | B1 * | 3/2004 | Neu et al. .......... 424/463 |
| 6,833,192 | B1 | 12/2004 | Caruso et al. |
| 2002/0039648 | A1 | 4/2002 | Horpel et al. |
| 2002/0172716 | A1 | 11/2002 | Walt et al. |
| 2002/0187197 | A1 | 12/2002 | Caruso et al. |
| 2004/0013738 | A1 | 1/2004 | Voigt et al. |
| 2004/0142341 | A1 | 7/2004 | Schmitt et al. |
| 2006/0251701 | A1 | 11/2006 | Lynn et al. |
| 2007/0020469 | A1 | 1/2007 | Wood et al. |

FOREIGN PATENT DOCUMENTS

| CA | 2012311 | 9/1990 |
| DE | 43 12 970 A1 | 10/1994 |
| DE | 19812083 | 9/1999 |
| DE | 19907552 | 8/2000 |
| DE | 10121903 | 10/2002 |
| EP | 0127713 | 12/1984 |
| EP | 0127989 | 12/1984 |
| EP | 0152898 | 8/1985 |
| EP | 2153780 | 8/1985 |
| EP | 0188309 | 7/1986 |
| EP | 0336014 | 10/1989 |

(Continued)

OTHER PUBLICATIONS

Donath, et al, "Nonlinear hairy layer theory of electrophoretic fingerprinting applied to consecutive layer by layer polyelectrolyte adsorption onto charged polystyrene latex particles", Langmuir 1997, 13, 5294-5305.

(Continued)

*Primary Examiner* — Susan Tran
(74) *Attorney, Agent, or Firm* — Fanelli Haag & Kilger PLLC

(57) ABSTRACT

The invention relates to capsules coated with a polyelectrolyte shell and methods for the production thereof.

7 Claims, 15 Drawing Sheets

FOREIGN PATENT DOCUMENTS

| | | |
|---|---|---|
| EP | 0392487 | 10/1990 |
| EP | 0 415 273 A2 | 3/1991 |
| EP | 0 443 428 A2 | 8/1991 |
| EP | 0 472 990 A2 | 3/1992 |
| EP | 540582 | 8/1994 |
| EP | 0 667 148 A1 | 8/1995 |
| EP | 0 823 331 A1 | 2/1998 |
| EP | 0972563 | 1/2000 |
| EP | 1116516 | 7/2001 |
| EP | 1 867 325 A2 | 12/2007 |
| GB | 1183403 | 3/1970 |
| GB | 2 135 954 A | 9/1984 |
| GB | 2 145 992 A | 4/1985 |
| JP | 60-190229 | 9/1985 |
| JP | 62-213839 * | 9/1987 |
| JP | 02-001307 | 1/1990 |
| JP | 02-290241 | 11/1990 |
| JP | 03-137152 | 6/1991 |
| JP | 07-213889 | 8/1995 |
| JP | 07-251003 | 10/1995 |
| JP | 08-169982 | 7/1996 |
| JP | 09-012938 | 1/1997 |
| JP | 09-077605 | 3/1997 |
| JP | 09-208440 | 8/1997 |
| WO | WO 92/00998 | 1/1992 |
| WO | WO 92/05778 | 4/1992 |
| WO | WO 95/26714 | 10/1995 |
| WO | WO 96/02136 | 2/1996 |
| WO | WO 96/18498 | 6/1996 |
| WO | WO 96/30409 | 10/1996 |
| WO | WO 98/14180 | 4/1998 |
| WO | WO 98/47948 | 10/1998 |
| WO | WO 99/47252 | 9/1999 |
| WO | WO 99/47253 | 9/1999 |
| WO | WO 00/03797 | 1/2000 |
| WO | WO 01/51196 | 7/2001 |
| WO | WO 01/64330 | 9/2001 |
| WO | WO 03/090920 | 11/2003 |
| WO | WO 2004/030648 | 4/2004 |
| WO | WO 2004/030649 | 4/2004 |
| WO | WO 2005/032512 | 4/2005 |
| WO | WO 2005/089825 | 9/2005 |

OTHER PUBLICATIONS

Caruso, et al. "Influence of Polyelectrolyte Multilayer coatings on Foerster Resonance Energy Transfer Between 6-carboxyfluorescein and Rhodamine B-Labeled Particles in Aqueous solution", Jour.of Physical Chem. (Feb. 1998).
Wang, et al., "Polyelectrolyte-Coated Colloid Spheres as Templates for Sol-Gel Reactions", Chem Mater., 2002, vol. 14, 1909-1913.
Written Opinion of the International Searching Authority for International Application No. PCT/EP2008/057434, Nov. 26, 2009.
A.S. Michaels, "Polyelectrolyte Complexes", J. Indust, & Eng. Otern., Oct. 1965, 57(10), 1965, pp. 32-40.
Petrak K., "Review: Polyelectrolyte Complexes in Biomedical Application", J. Bioactive & Compatibie Biopolymers, 1986, vol. 1, pp. 202-219.
Johansen, et al., "Bnmobilization of Yeast Cells Binternal Gelation of Alignate", Enzyme Microb. Technol., 1986, vol. 8, pp. 145-148.
C.A. Finch, "Polymers for Microcapsule Walls", Chemistry and Industry, 1985, pp. 752-756.
Encyclopedia of Chemical Technology "Microencapsulation", 1981, vol. 15, Third Edition, pp. 1A-25A.
C.E. Camp, et al., "Calcium Alginate-Immobiiized Hepatic Microsomes: Effect of NADPH Cofactor on Oxidation Rates", Enzyme Micro. Technol., 1987, vol. 9, pp. 685-689.
Donath, et al., "Novel Hollow Polymer Shells by Colloid-Templated Assembly of Polyelectrolytes", Angew. Chem. int. Ed., 1998, vol. 37, No. 16. pp. 2202-2205.
Kim, et al., "Effect of Organic Solvent on the Permeability and Stiffness of Polyelectrolyte Multilayer Microcapsules", Macromolecules, 2005, vol. 38, pp. 5214-5222.
Decher G., et al. "Buildup of Ulrathin Multilayer Films by a Self-Assembly Process: Ill. Consecutively Alternating Adsorption of Anionic and Cationic Polyelectrolytes on Charged Surfaces", Thin Solid Films, 1992, vol. 210-211, No. 1-2, Part 2, pp. 831-835.
Meldrum, et ale "Magnetoferritin: In Vitro Synthesis of a Novel Magnetic Protein", Science, 1992, vol. 257, pp. 522-523.
Caruso, et al., "Investigation of Electrostatic Interactions in Polyelectrolyte Multilayer Films: Binding of Anionic Fluorescent Probes to Layers Assembled onto Colloids", Macromolecules, 1999, vol. 32, pp. 2317-2328.
Kawahashi, et al., "Preparation and Properties of Uniform Coated Colloidal Particles", Journal of Colloid and Interface Science, 1990, vol. 138, No. 2,pp. 534-542.
Philipse et al., "Magnetic Silica Dispersions: Preparation and Stability of Surface-Modified Silica Particles with a Magnetic Core", Langmuir, 1994, vol. 10, pp. 92-99.
German Office Action date Mar. 7, 2006.
German Office Action date Nov. 3, 2004.
Dahne, et al., "Fabrication of Micro Reaction Cages with Tailored Properties", J. Am. Chem. Soc., 2001, vol. 123, pp. 5431-5436.
Antipov, et al., Polyelectrolyte Multilayer Capsule Permeability Control, Colloids and Surfaces A: Physicochemical and Engineering Aspects, 2002, vols. 198-200, pp. 535-541.
Shchukin, et al., "Smart Inorganic/Organic Nanocornposite Hollow Microcapsules", Angew. Chem. Int. Ed., 2003, vol. 42, pp. 4472-4475.
Volodkin, et al., "Matrix Polyelectrolyte Microcapsules: new System for Macromolecule Encapsulation", Langmuir, 2004, vol. 20(8), pp. 3398-3406.
Donath, et al., "Novel Hollow Polymer Shells by Colloid Templated Assembly of Polyelectrolytes", Angew. Chem, Int. Ed. 1998, vol. 37(16), pp. 2201-2205.
English Translation in Part of German Office Action dated Mar. 26, 2009.
Ibarz, et al., "Smart Micro- and Nanocontainers for Storage, Transport, and Release", Adv. Mater, 2001, vol. 13(17), pp. 1324-1327.
German Office Action dated Mar. 26, 2009.
Mohwald, et al., "Smart Capsules" Multilayer Thin Films Ed., Schlenoff, New York 2003, pp. 363-392.
Radtchenko, et al., Incorporation of Macromolecules Into Polyelectrolyte Micro- and Nanocapsules Via 4 Surface Controlled Precipitation on Colloidal Particles, Colloids and Surfaces A Physicochemical and Engineering Aspects, 2002, vol. 202, pp. 127-133.
International Search Report for International Application No. PCT/EP2008/057434, Nov. 26, 2009.
International Search Report for International Application No. PCT/EP2005/002810, 0812312005.
Dahne, et al., "Nanoengineered Capsules with Specific Layer Structures", Encyclopedia of Nanoscience and Nanotechnology, Marcel Dekker, Inc., 2004, pp. 2355-2367.
Unverified English Language Translation of Decsion of Refusal in Japanese Patent Application No. 2000-536480, Aug. 27, 2010, 3 pages.
Tarnotsu Kondo, "Microcapules <their functions and applications>," JP, Zaidan Hojin Nippon Kikaku Kyokai, Mar. 20, 1991, pp. 122-123, 272.
Sukhorukov, et al. "Stepwise Polyelectrolyte Assembly on Particle Surfaces: a Novel Approach to Colloid Design", *Polym. Adv. Technol.* 9, (1998) pp. 759-767.
Sukhorukov, et al. "Layer-by-layer self assembly of polyelectrolytes on colloidal particles", *Colloids and Surfaces*, 137 (1998) pp. 253-266.

* cited by examiner

A: control
B: 11 layers
C: 21 layers

US 8,168,226 B2

PRODUCTION OF NANOCAPSULES AND MICROCAPSULES BY LAYER-WISE POLYELECTROLYTE SELF-ASSEMBLY

This application is a continuation application of U.S. Ser. No. 10/376,386 filed Feb. 27, 2003 now U.S. Pat. No. 7,101,575, incorporated herein by reference, which is a continuation of U.S. Ser. No. 09/646,742 filed Nov. 6, 2000 now abandoned, which is a 371 of PCT/EP99/01855 filed Mar. 19, 1999, which claims priority from German Patent Application No. 198 12 083.4 filed Mar. 19, 1998, European Patent Application No. 98 113 181.6 filed Jul. 15, 1998 and German Patent Application No. 199 07 552.2 filed Feb. 22, 1999.

DESCRIPTION

The invention relates to nanocapsules and microcapsules which comprise a polyelectrolyte shell, to a method for the production of these capsules, and to the use thereof.

Microcapsules are known in various embodiments and are used in particular for controlled release and targeted transport of active pharmaceutical ingredients, and for protecting sensitive active ingredients such as, for example, enzymes and proteins (see, for example, D. D. Lewis, "Biodegradable Polymers and Drug Delivery Systems", M. Chasin and R. Langer, editors (Marcel Decker, New York, 1990); J. P. McGee et al., J. Control. Release 34 (1995), 77).

Microcapsules can be produced by mechanical-physical processes such as, for example, spraying and subsequent coating. However, the microcapsules obtainable in this way have a number of disadvantages. In particular, it is not possible with the known mechanical-physical processes to produce microcapsules with a size of <10 µm (diameter). On the contrary, it is possible to obtain only microcapsules with relatively large diameters, but the range of applications thereof is restricted because of their size. In addition, the known mechanical-physical processes do not result in a monodisperse capsule distribution but, on the contrary, result in a nonuniform distribution of capsules of varying size. This is also disadvantageous for many applications in which the size of the capsule is important.

Besides the mechanical-physical processes, also known for producing microcapsules are chemical processes. Thus, it is possible to produce microcapsules by interfacial polymerization or condensation or by polymer phase separation from a polymer/solvent mixture (B. Miksa et al., Colloid Polym. Sci. 273 (1995), 47; G. Crotts et al., J. Control. Release 35 (1995), 91; S. L. Regen et al., J. Am. Chem. Soc. 106 (1984), 5756). However, the microcapsules produced by known chemical processes also have a number of disadvantages. In particular, a high polydispersity, a nonuniform envelope and, frequently, a solidification of the core are to be observed. Another essential disadvantage of the known chemical processes derives from the use of organic solvents and polymerizable organic monomers, which leads to considerable restrictions on the active ingredients which can be used for encapsulation. In particular, the use, which is often made necessary thereby, of water-immiscible organic liquids as core material drastically limits the range of applications of such microcapsules, particularly in relation to proteins or enzymes.

Lipid liposomes are another system which has been used for encapsulating inorganic and organic materials (D. D. Lasic, "Liposomes: From Physics to Applications" (Elsevier, Amsterdam, 1993); S/L. Regen et al., J. Am. Chem. Soc. 106 (1984), 2446). The encapsulation of active ingredients in lipid liposomes makes it possible to produce microcapsules under relatively mild conditions, which is why liposomes are used as carrier systems for various active pharmaceutical and cosmetic ingredients. The biological, chemical and mechanical stability of such liposome capsules is, however, very low, which limits the general utilizability of such capsules. Another disadvantage is represented by the low permeability of liposome capsules, in particular for polar molecules, which prevents exchange of matter with the surrounding medium.

In another process for producing microcapsules there is initial formation of mixtures of the material to be entrapped and of a polyelectrolyte constituent which can be solidified with, for example, $Ca^{2+}$ ions. This mixture is introduced in the form of very small droplets into a $Ca^{2+}$ bath to form a gel structure which can then be surrounded with a polyelectrolyte capsule in further process steps. A further development of such processes is described in DE 33 06 259 A1, where the use of $Ca^{2+}$ can be dispensed with. The main disadvantage of these processes is that the lower limit of size of the microcapsules which can be produced is about 50 µm (diameter), and the wall thickness of the resulting microcapsules is at least 100 nm.

DE-A-40 26 978 describes a process for coating sheet-like supports, with a support being modified so that it has ions or ionizable compounds with the same charge over the entire area, and one or more layers of organic materials which contain in each layer ions of the same charge being applied from a solution of such organic materials to the modified support, where the organic material for the first layer has ions with the opposite charge to the charge of the ion-modification of the support, and in the case of several layers there is alternate application of further layers, with ions having the opposite charge to the previous one in each case, in the same manner as the first layer. The supports disclosed are inorganic or organic support materials having an even surface. There is no reference to the use of microparticles as support materials or to a disaggregation of the support materials after the coating.

One object of the invention is therefore to provide capsules with a small diameter in which it is possible to entrap materials such as, for example, macromolecules, precipitates, liquids or gases. It was further intended that the capsules have a high stability and shells which have a low wall thickness and which are permeable in particular to ions and small molecules.

The object is achieved according to the invention by capsules having a polyelectrolyte shell and a diameter of up to 10 µm or more.

It has been found, surprisingly, that coating of template particles with a polyelectrolyte shell and, where appropriate, subsequent disintegration of the template particles make it possible to obtain capsules with defined inner and outer shell properties and with selectively controllable permeability properties. A polyelectrolyte shell means a shell having a content of polyelectrolytes. The polyelectrolyte shell is preferably at least 50%, in particular at least 60% and particularly preferably at least 80% composed of polyelectrolytes. The capsules according to the invention allow the entrapment also of sensitive molecules under mild conditions, for example in aqueous solutions. The capsule wall is a polyelectrolyte shell which makes exchange of matter, in respect of low molecular weight substances and ions, with the surroundings possible, but, at the same time, retains macromolecular substances. This separating function of the polyelectrolyte shell has the effect on the one hand that active ingredients entrapped in the capsule where appropriate are retained, but on the other hand that no interfering macromolecular substances can get into the capsule from outside. In this way, active ingredients are efficiently protected, even without the addition of preservative substances, from biological degradation processes. The chemical and physical properties of the polyelectrolyte shell serving as capsule wall can be controlled within wide limits by the structure and composition of the shell and the surrounding parameters. Thus, the novel capsules can serve, for example, as transport chambers, in which case the parameters of the outer layer determine transport to preset target sites, for example in the body.

The novel capsules comprise microcapsules with a diameter of from 1 µm to 50 µm, preferably $\leq$10 µm, particularly preferably $\leq$5 µm and most preferably $\leq$2 µm, and nanocapsules with a diameter of $\geq$10 nm to <1000 nm.

The shell of the capsules has a plurality of polyelectrolyte layers. Polyelectrolytes mean in general polymers with groups which are capable of ionic dissociation and may be a constituent or substituent of the polymer chain. The number of these groups capable of ionic dissociation in polyelectrolytes is normally so large that the polymers are water-soluble in the dissociated form (also called polyions). In this connection, the term polyeletrolytes also means ionomers with which the concentration of ionic groups is insufficient for water solubility but which have sufficient charges to enter into self-assembly. The shell preferably comprises "true" polyelectrolytes. Depending on the nature of the groups capable of dissociation, polyelectrolytes are divided into polyacids and polybases. On dissociation of polyacids there is formation of polyanions, with elimination of protons, which can be both inorganic and organic polymers. Examples of polyacids are polyphosphoric acid, polyvinylsulfuric acid, polyvinylsulfonic acid, polyvinylphosphonic acid and polyacrylic acid. Examples of the corresponding salts, which are also referred to as polysalts, are polyphosphate, polysulfate, polysulfonate, polyphosphonate and polyacrylate.

Polybases contain groups able to take up protons, for example by reaction with acids to form salts. Examples of polybases with groups capable of dissociation located on the chains or laterally are polyethyleneimine, polyvinylamine and polyvinyl-pyridine. Polybases form polycations by taking up protons.

Polyelectrolytes suitable according to the invention are both biopolymers such as, for example, alginic acid, gum arabic, nucleic acids, pectins, proteins and others, and chemically modified biopolymers such as, for example, ionic or ionizable polysaccharides, for example carboxymethylcellulose, chitosan and chitosan sulfate, ligninsulfonates, and synthetic polymers such as, for example, polymethacrylic acid, polyvinylsulfonic acid, poly-vinylphosphonic acid and polyethyleneimine.

It is possible to employ linear or branched polyelectrolytes. The use of branched polyelectrolytes leads to less compact polyelectrolyte multifilms with a higher degree of porosity of the walls. To increase the capsule stability it is possible to crosslink polyelectrolyte molecules within or/and between the individual layers, for example by crosslinking amino groups with aldehydes. A further possibility is to employ amphiphilic polyelectrolytes, for example amphiphilic block or random copolymers with partial polyelectrolyte characteristics to reduce the permeability to small polar molecules. Such amphiphilic copolymers consist of units differing in functionality, for example acidic or basic units on the one hand, and hydrophobic units on the other hand, such as styrenes, dienes or siloxanes etc., which can be arranged as blocks or randomly distributed over the polymer. It is possible by using copolymers which change their structure as a function of the external conditions to control the permeability or other properties of the capsule walls in a defined manner. Suitable examples thereof are copolymers with a poly(N-isopropylacrylamide) content, for example poly(N-isopropylacrylamide-acrylic acid), which change their water solubility as a function of the temperature, via the hydrogen bonding equilibrium, which is associated with swelling.

The release of entrapped active ingredients can be controlled via the dissolution of the capsule walls by using polyelectrolytes which are degradable under particular conditions, for example photo-, acid-, base-or salt-labile polyelectrolytes. A further possibility for particular possible applications is to use conducting polyelectrolytes or polyelectrolytes with optically active groups as capsule components.

It is possible by a suitable choice of the polyelectrolytes to adjust the properties and composition of the polyelectrolyte shell of the novel capsules in a defined manner. In the particular case of polyelectrolyte shells built up layer-wise it is possible to vary the composition of the shells within wide limits by the choice of the substances for building up the layers. There are in principle no restrictions on the polyelectrolytes or ionomers to be used as long as the molecules used have a sufficiently high charge or/and have the ability to enter into a linkage with the underlying layer via other interactions such as, for example, hydrogen bonding and/or hydrophobic interactions.

Suitable polyelectrolytes are thus both low molecular weight polyelectrolytes or polyanions and macromolecular polyelectrolytes, for example polyelectrolytes of biological origin.

Of particular importance for the use of the capsules is the permeability of the shell wall. As already stated above, the large number of polyelectrolytes available makes it possible to produce a large number of shell compositions with different properties. In particular the electrical charge of the outer shell can be adapted to the purpose of use. In addition, the inner shell can be adapted to the active ingredients encapsulated in each case, whereby it is possible to achieve, for example, stabilization of the active ingredient. It is also possible in addition to influence the permeability of the shell wall through the choice of the polyelectrolytes in the shell and through the wall thickness and the surrounding conditions. This makes it possible to design the permeability properties selectively and to change these properties in a defined manner.

The permeability properties of the shell can be further modified by pores in at least one of the polyelectrolyte layers. Such pores may be formed by the polyelectrolytes themselves if chosen suitably. Besides the polyelectrolytes, however, the shell may also comprise other substances in order to achieve a desired permeability. Thus, in particular, the permeability for polar components can be reduced by incorporation of nanoparticles with anionic or/and cationic groups or of surface-active substances, such as, for example, surfactants or/and lipids. Incorporation of selective transport systems such as, for example, carriers or channels into the polyelectrolyte shell, in particular in lipid layers, makes it possible accurately to adapt the transverse transport properties of the shell to the particular purpose of use. The pores or channels in the shell wall can be opened or closed specifically by chemical modification or/and changing the surrounding conditions. Thus, for example, a high salt concentration in the surrounding medium leads to very high permeability of the shell wall.

A particularly preferred modification of the permeability of polyelectrolyte shells can be achieved by depositing lipid layers or/and amphiphilic polyelectrolytes on the polyelectrolyte shell after disintegration of the template particles. It is possible in this way very greatly to reduce the permeability of the polyelectrolyte shells for small and polar molecules.

Examples of lipids which can be deposited on the polyelectrolyte shells are lipids which have at least one ionic or ionizable group, for example phospholipids such as, for example, dipalmitoylphosphatidic acid or zwitterionic phospholipids such as, for example, dipalmitoyl-phosphatidylcholine or else fatty acids or corresponding long-chain alkylsulfonic acids. It is possible on use of zwitterionic lipids to deposit lipid multilayers on the polyelectrolyte shell. Further polyelectrolyte layers can then be deposited on the lipid layers.

The novel capsules preferably have a shell wall thickness from 2 to 1000 nm, in particular 2 to 100 nm, for example of from 5 to 8 nm. The thickness of the shell wall depends on the number of layers of the polyelectrolyte shell. The capsules preferably contain from 2 to 40, preferably 2 to 20, for example 3 to 10, layers. However, the capsules may also contain a larger number of layers, i.e. polyelectrolyte layers and, where appropriate, other layers such as lipid layers.

The novel capsules are further distinguished by their monodispersity. Thus, it is possible to obtain a composition with a capsule distribution in which the proportion of capsules with a deviation of >50% from the average diameter is less than 20%, preferably less than 10% and, particularly preferably, less than 1%.

The capsules are very stable to chemical, biological, mechanical and thermal stresses. The capsules can, where appropriate with entrapped active ingredients, be dried, frozen or/and freeze-dried without impairing their properties. Intact capsules are obtained again after thawing or resuspension in water.

Drying or freeze-drying of the capsules results in a composition in powder form which can be resuspended in suitable solvents, in particular in aqueous solutions. The invention therefore further relates to a composition comprising dried capsules. The drying can be carried out by known methods, in particular at elevated or reduced temperature or/and reduced pressure.

The invention further relates to a method for the production of capsules coated with a polyelectrolyte shell, comprising the steps:
a) preparing an aqueous dispersion of template particles of suitable size and
b) producing a shell around the template particles by application of polyelectrolytes to the template particles.

Firstly an aqueous dispersion of template particles of suitable size is prepared. The size of the capsules is fixed by the size of the template particles. Then preferably a plurality of polyelectrolyte layers is applied to the template particles to form an enveloped template particle. The shape of the shell depends directly on the shape of the template particles.

For the application of the polyelectrolyte layers to the template there is preferably production of a dispersion of the template particles in an aqueous solution. Polyelectrolyte molecules from which the first layer is to be built up are then added to this dispersion. These polyelectrolyte molecules may have the same or the opposite charge as the surface of the template particles. The amount of the added polyelectrolyte molecules is chosen so that all the material is required for building up the first layer, or an excess is used. In the latter case, removal of the excess polyelectrolyte molecules not required to build up the first layer is expedient before addition of oppositely charged polyelectrolyte molecules for building up the second layer. The polyelectrolyte molecules can be removed by known methods, in particular centrifugation, filtration or/and dialysis. Removal by membrane filtration as described hereinafter is particularly preferred. Subsequently there is further alternate application of oppositely charged layers of polyelectrolyte molecules, it being possible to choose for each layer with the same charge identical or different polyelectrolyte species or mixtures of polyelectrolyte species. The number of layers can in principle be chosen as desired. Besides polyelectrolyte molecules it is also possible to deposit other substances such as nanoparticles, surface-active substances or/and lipids on the template particles.

Template particles which can be employed are both inorganic materials, for example metals, ceramics, oxides or salt crystals, and organic materials such as polymer latices or melamine-formaldehyde particles, lipid vesicles or biological template particles. Emulsion droplets are likewise suitable. The size of the template particles can be up to 50 µm—especially on use of biological template materials. However, in most cases, the template particles are up to 10 µm, particularly preferably from 5 nm to 5 µn, in size. The shape of the template particles is not critical. Both spherical and anisotropic particles can be coated.

It is also possible to employ aggregates of subparticles as initial cores (template particles) for coating with polyelectrolytes. These aggregates can, where appropriate, be employed in the preshaped or preformed state. Such a preforming can be achieved, for example, by applying external electrical direct or/and alternating fields or magnetic fields to suspensions with subparticles. The shape of the capsules can be determined by preshaped aggregates. It is additionally possible to obtain such aggregates with a great uniformity with regard to the size distribution (monodispersity). However, non-preshaped aggregates are also just as suitable. Spherically shaped aggregates are of particular interest.

The template particles used do not necessarily have to be charged in order to make self-assembly of polyelectrolyte layers possible. On the contrary, it is possible to apply to uncharged cores a charged precursor film which is bound to the template particles by other interactions, for example hydrophobic interactions.

After application of the required number of polyelectrolyte layers, the enveloped template particles can, if desired, be disintegrated, in particular comminuted or disaggregated. This leaves behind "empty" capsules with a polyelectrolyte shell. The disaggregation of the template particles is carried out under conditions in which the shells remain intact. A disaggregation can take place, for example, thermally or chemically depending on the material chosen for the template particles. The low molecular weight core ingredients produced in the disaggregation can reach the outside through the pores in the shell. This results in capsules with polyelectrolyte shells which contain an "empty" core. Other coating substances can be applied to the empty polyelectrolyte molecules.

It is possible after disintegration of the template particles for a liquid phase to be present inside the capsule shell. It is possible in principle for the capsules to contain any liquid in their interior, for example an aqueous liquid, in particular an aqueous salt solution or water, or else organic solvents, in particular water-immiscible solvents such as alcohols or hydrocarbons having at least 4 C atoms. The capsules may also contain solids or gases in their interior.

It is preferred to employ partially crosslinked melamine-formaldehyde particles as template particles which can be disaggregated by adjusting the pH in the medium containing the enveloped particles to an acidic value, for example $\leq 1.5$, while the shell layer itself remains intact. The partially crosslinked melamine-formaldehyde particles can also be disaggregated by chemical reactions, in particular by sulfonation in aqueous media. The sulfonating agents preferably used are alkali metal sulfates, alkali metal hydrogen sulfites and other water-soluble salts of sulfurous acid. Other examples of template particles which can be disaggregated are soluble polymer cores, for example urea-formaldehyde particles, or salt crystals.

It is additionally possible to use as template materials, for example, cells, for example eukaryotic cells such as, for example, mammalian erythrocytes or plant cells, single-celled organisms such as, for example, yeasts, bacterial cells such as, for example, *E. coli* cells, cell aggregates, subcellular particles such as, for example, cellular organelles, pollen, membrane preparations or cell nuclei, virus particles and aggregates of biomolecules, for example protein aggregates such as, for example, immune complexes, condensed nucleic acids, ligand-receptor complexes etc. The method according to the invention is also suitable for encapsulating living biological cells and organisms. Likewise suitable as templates are aggregates of amphiphilic materials, in particular membrane structures such as, for example, vesicles, for example liposomes or micelles, and other lipid aggregates.

The disintegration of biological template particles can take place by adding lytic reagents. Lytic reagents suitable for this purpose are those able to disaggregate biological materials such as proteins or/and lipids. The lytic reagents preferably comprise a deproteinizing agent, for example peroxo compounds such as, for example, $H_2O_2$ or/and hypochlorite compounds such as, for example, sodium or potassium hypochlorite. Surprisingly, disintegration of the template particles takes place within a short incubation time, for example 1 min to 1 h, at room temperature. The disintegration of the template particles is substantially complete because no residues of the particles are detectable even on examination of the remaining shells under the electron microscope. It is also possible on incorporation of biological polyelectrolytes into the shell for empty layers to be produced within the polyelectrolyte shell.

The fragments formed on disintegration of the template particles, for example in the case of partially crosslinked melamine-formaldehyde particles the oligomers produced on disaggregation, can escape from the interior of the capsules to the outside through pores, in particular nanopores, in the shell wall. They can then, if required, be removed from the capsules. This removal can be carried out by methods known to the skilled worker, for example by dialysis, filtration or/and centrifugation. However, removal of template particle fragments is often unnecessary. The capsule can be used even without a removal step.

It is also possible with the novel method to produce capsules with entrapped active ingredients or capsules for entrapping active ingredients. Loading of the interior with small molecules can take place by varying the permeability of the shell as a function of the external physical and chemical parameters. A state of high permeability is set up for the loading. The entrapped material is then retained by altering the external parameters or/and closing the pores, for example by condensation of the shell or chemical modification of the pores or channels.

The active ingredients may be both inorganic and organic substances. Examples of such active ingredients are catalysts, in particular enzymes, nanoparticles, active pharmaceutical ingredients, polymers, dyes such as, for example, fluorescent compounds, sensor molecules, i.e. molecules which react detectably to a change in surrounding conditions (temperature, pH), crop protection agents and aroma substances. Since the capsules may comprise aqueous solutions in their core, it is possible for even sensitive molecules to be entrapped under mild conditions.

On entrapment of catalysts, for example ceramic and/or metallic particles or enzymes, in the capsules it is possible for the catalysts either to be adsorbed on the inside of the capsule wall or to be present as free molecules in the capsule interior, so that a virtually loss-free use of the catalysts is made possible. The catalyst-containing capsules can be retained or recovered more easily than the free catalyst. Contamination of the catalysts is substantially precluded by the protecting and separating function of the capsule shell relative to the surrounding medium. In particular, the permeability properties of the capsule walls prevent catalysts entrapped inside the capsules having their activity blocked or inhibited by macromolecular substances, while entry of substrate and exit of products is possible.

The capsules may also comprise entrapped active pharmaceutical ingredients. In this case, the capsule acts in particular as transport vehicle in order to stabilize the active pharmaceutical ingredients, protect them from degradation or/and transport them to the required site of action in the body. Specific transport can be achieved by selection of the surface properties of the outer shell.

The polyelectrolyte shell of the capsules is preferably permeable for low molecular weight substances but prevents macromolecules from passing through. The shell wall thus represents a barrier to microorganisms and external digestive enzymes secreted by them. It is therefore possible for biodegradable substances to be entrapped in the novel capsules without preservatives being necessary for stabilization.

The capsules can also be used as reaction chambers for chemical reactions or as precipitation or crystallization templates, in which case it is possible to employ empty capsules or capsules comprising an active ingredient or catalyst. Because of the fact that the permeability of the capsule walls can be controlled so that, for example, they allow low molecular weight substances to pass through but substantially retain macromolecules, the high molecular weight products produced in a chemical reaction, for example polymers produced in a polymerization, can be retained in the interior in a simple way during the synthesis. The reaction product synthesized at the same time in the external medium can be removed, subsequently or even during the reaction, for example by centrifugation or/and filtration.

The supply of the reaction substrate can be controlled during the reaction by the diffusion through the capsule walls. New ways of intervening in the progress of reactions emerge from this. The external medium can be replaced, for example continuously by filtration or for example also suddenly by centrifugation, the polymerization reaction can be stopped as desired by removing the substrate or the monomer can be replaced. It is thus possible to produce defined copolymers or multipolymers in a novel way. Since the progress of the reaction can be controlled by the monomer supply through the permeation, it is possible to produce in the capsules products with novel and different molecular weight distributions, for example highly monodisperse products. Polymers synthesized inside capsules can be detected, for example, by NMR, by IR, spectroscopically by titration with fluorescent dyes and by confocal microscopy. The gain in mass and thus the kinetics of the reaction can be followed by single particle light scattering.

On use of anisotropic capsules for packaging active ingredients or as reaction chambers, for example for syntheses or precipitation processes, and, where appropriate, subsequent disaggregation of the template shells, it is possible to produce particle compositions as dispersions with predetermined shapes and forms. The invention thus also relates to anisotropic particle compositions which are obtainable by encapsulating active ingredients in a polyelectrolyte shell, for example by synthesis or precipitation and subsequent removal of the template, for example by thermal or chemical treatment. These anisotropic particles preferably have the shape of the structures used as template. Anisotropic particles can be moved, for example rotated or aligned, by applying fields. It is possible in this way to produce dispersions with switching properties.

A further possibility is to use the capsules for introducing organic liquids such as, for example, alcohols or hydrocarbons, for example hexanol, octanol, octane or decane, or for encapsulating gases. Such capsules filled with an organic, water-immiscible liquid can also be employed for chemical reactions, for example polymerization reactions. The monomer can thus be specifically concentrated in the interior of the capsules through its distribution equilibrium. It is possible where appropriate for the monomer solution to be encapsulated in the interior even before the start of the synthesis.

However, it is also possible to encapsulate active ingredients which are unable, because of their size, to penetrate through the polyelectrolyte shell. For this purpose, the active ingredient to be entrapped is coupled to or immobilized on the template particle or is encapsulated or taken up by the template particle, for example by phagocytosis or endocytosis in the case of living cells or by encapsulation of nanoparticles in soluble template materials. After disintegration of the template particles, the active ingredient is released inside the polyelectrolyte shell. It is expedient to choose the conditions for disintegration of the template particle in this case so that no unwanted decomposition of the active ingredient takes place.

Coupling of the active ingredient to the template can take place directly, but can also be brought about by a linkage mediator. The linkage mediators preferably used are molecules which can be degraded or broken down under particular conditions. Polylactic acid is particularly preferably used as linkage mediator. For this purpose, the active ingredient is immobilized on the template particle, for example a partially crosslinked melamine-formaldehyde particle, by means of the linkage mediator, in particular polylactic acid. In this way the active ingredient to be entrapped itself becomes a constituent of the layer structure in the coating of the core. After disaggregation of the template particles and, where appropriate, degradation of the linkage molecules, the active ingredient is released inside the shell. It is possible with this method to entrap any active ingredients in the shell, in particular nanoparticles and nonbiological macromolecular components and, preferably, biological macromolecules such as, for example, proteins, in particular enzymes.

A further possibility is to immobilize cationic polymers or particles in the shell for example with 4-pyrenesulfonate (4-PS). These particles are then released inside the shell by dissolving out 4-PS in salt solutions.

However, incorporation of active ingredients in the interior surrounded by the shells can also be carried out by previous introduction of the active ingredients into the template particles on use of reversible microgels as template particles. Thus, for example, the use of partially crosslinked methylolmelamine cores before the coating makes it possible to incorporate in swollen cores substances which are entrapped in the core after a reversible shrinkage.

The capsules can also be immobilized on a surface. Adjustment of the charge on the outer layer and the free functionalizability of the external shell makes immobilization of the capsules which is independent of the condition of the entrapped molecules possible. This opens up numerous possible applications, especially in the area of sensor systems and surface analysis. This may entail the polyelectrolyte-coated template particles adhering to a surface, and the template particles then being dissolved out of the previously immobilized coated cores in order to form immobilized capsules. However, it is equally possible for the dissolving of the cores to take place before deposition on the surface.

The capsules can be employed in numerous areas of application, for example sensor systems, surface analysis, as emulsion carriers, microreaction chambers such as, for example, for catalytic processes, polymerization, precipitation or crystallization processes, in pharmacy and medicine, for example for targeting active ingredients or as ultrasonic contrast agents, in food technology, cosmetics, biotechnology, information technology, the printing industry (encapsulation of dyes), photographic industry and for veterinary medicine or agriculture (active ingredients for animal health, active ingredients for agriculture or horticulture). The capsules can further be employed for building up microcomposites or nanocomposites, i.e. materials consisting of at least two different materials and having a microscopic or nanoscopic arrangement.

On use of the capsules as reaction chambers it is possible for the low molecular weight substances such as, for example, precursors and products to permeate through the shell walls, whereas the catalysts, for example, are entrapped. On use of microcapsules or nanocapsules loaded with catalysts, the capsules being packed, for example, in a column, considerably more catalyst is available for the reaction than with conventional surface-bound catalysts, because the size of the surface is limiting there. It is a particular advantage that the catalyst inside the capsule does not have to be removed again from the production by elaborate methods. In addition, the useful life of the catalysts is improved because macromolecular substances, in particular bacteria and fungi, cannot get through the shell walls. This reduces the high sterility demands placed on many processes, which opens up many industrially simple applications of biological catalysts.

Sensor molecules can also be entrapped in the capsules. These may be enzymes which, in the presence of a substrate, form products which can be detected optically or in another way, for example colored or fluorescent products, under suitable conditions. However, it is also possible to entrap electrically active sensor molecules, in particular oxidizable or reducible substances, in which case the capsules can be immobilized on electrodes. In this case, a particular advantage besides the protective function of the capsules is that the sensor molecule does not come into direct contact with the electrode.

The capsules can also be used for producing crystals or amorphous precipitates of organic or inorganic materials or for entrapping organic or inorganic crystals or amorphous precipitates. The capsules are preferably used as crystallization or precipitation chamber or templates for producing in particular monodisperse crystals or precipitates. A high degree of monodispersity can be obtained with the novel capsules because the maximum size of the entrapped particles is limited by the size of the capsules. Chemical groups on the inner shell wall can be used as crystallization nuclei. For this purpose, molecules having side chains which favor crystal growth are used in the innermost layer in the layer-wise building up of the shell of the capsules. Thus, for example, it is possible to attach polyphosphates to the inside of the shell in order to form $CaCo_3$ in the interior. It is beneficial to use polyelectrolytes which suppress crystal growth, for example amines, as outermost layer of the polyelectrolyte shell of the capsules.

The capsules can also be used to build up microcomposites or nanocomposites. Microcomposites and nanocomposites are materials consisting of at least two different materials and having a microscopic or nanoscopic arrangement. Such composites often imitate products present in nature, such as, for example, mussel shells which, as nanocomposites, consist of ordinary lime and protein molecules. Such composites have surprisingly great strength while being of low weight.

Ordered macroscopic structures can be built up by the assembling.

Anisotropic shells produced using anisotropic template particles, for example biological template particles, allow, in conjunction with, for example, crystallization or/and precipitation, composites with anisotropic properties to be produced. Thus, for example, magnetic ellipsoids can be produced for example by packing with magnetic particles or/and by adsorption of magnetic nanoparticles to the poly-electrolyte shell. These anisotropic particles show an orientation in the magnetic field, which makes it possible to change the optical properties of a particle suspension rapidly (magneto-optical switch). An analogous process is possible with ferroelectric particles. It is possible with the aid of these particles, for example, to stimulate small paddle wheels to pump with a rotating field (micromechanics). It is also possible to heat anisotropic particles by dissipation. This can be used to produce extremely localized heat sources which can be moved with electrical or with magnetic fields. This makes it possible to produce local hyperthermia effects. A further possibility is to produce, by ordered alignment of anisotropic particles, composite materials with a hierarchic structure and interesting macroscopic physical anisotropic properties.

As previously stated, the permeability of the polyelectrolyte shell can be controlled by modifications, for example application of lipid layers. This can be utilized for pharmaceutical applications by applying lipids to the shell after the encapsulation of polar low molecular weight substances, in order in this way to reduce the permeability of the shell for the encapsulated substances. The encapsulated substance is then able to escape only slowly through the lipid layer at a rate which is constant over a long period, which is often desirable for pharmacological administrations.

It is possible by the encapsulation and subsequent disaggregation of templates to produce accurate three-dimensional impressions of template particles. Block crosslinking of the polyelectrolyte shells results in mesoporous materials with a monodisperse accurate pore distribution. These materials have a large internal surface area together with great strength, which make them excellent filter substances for industrial purposes. Mesoporous materials with predetermined pores can be produced by selection of the templates (shape and size).

It is, of course, possible by varying the materials used to produce the polyelectrolyte shells also to vary the surface chemistry within wide limits.

Finally, the polyelectrolyte shells can also be used to produce pH gradients between the interior of the shell and the volume surrounding the shell. This pH gradient can in turn be utilized for efficient loading of the shells with active ingredients.

Yet a further aspect of the invention is the application of a plurality of successive layers to a carrier by a filtration method. This method makes it possible to produce, in a simple manner and on a large scale, capsules coated with polyelectrolyte molecules. Surprisingly, even sensitive template particles such as biological cells can be coated by a filtration method.

The invention thus relates to a method for application of a plurality of layers of coating substances to template particles, comprising the steps:

(a) contacting the template particle with a first coating substance in a fluid, preferably aqueous reaction medium in a reaction chamber which is limited on at least one side by a filtration membrane, under conditions with which a layer of the first coating substance is formed on the template particle, (b) draining at least part of the reaction medium with, where appropriate, excess first coating substance present therein through the filtration membrane into a filtrate chamber, there preferably being essentially complete draining of the excess first coating substance, (c) contacting the template particle with a second coating substance in a fluid reaction medium in a reaction chamber which is limited on at least one side by a filtration membrane, under conditions with which a layer of the second coating substance is formed on the template particle, (d) draining at least part of the reaction medium with, where appropriate, excess second coating substance present therein through the filtration membrane into a filtrate chamber, there preferably being essentially complete draining of the excess second coating substance, and (e) where appropriate repeating steps (a) and (b) or/and (c) and (d) a plurality of times.

The first and second coating substances preferably used are polyelectrolyte species, or mixtures of polyelectrolyte species, of opposite charge in each case. It is also possible to use nanoparticles, amphiphilic polyelectrolytes, lipids or/and surfactants as coating substances.

The template particles are preferably selected from particles having a diameter of up to 50 μm, in particular up to 10 μm. Particles capable of disaggregation as previously mentioned, for example partially crosslinked melamine-formaldehyde particles, biological particles or aggregates of biological or/and amphiphilic materials, in particular biological aggregates such as cells, cell aggregates, virus particles etc., are preferably used.

In order to make complete removal of excess coating substance possible after a coating step, a washing medium, for example water or an aqueous buffer solution, is introduced into the reaction chamber during or/and after step (b) or/and (d). Addition of the washing medium takes place, especially with sensitive template particles such as biological aggregates, in such a way that the volume of the medium present in the reaction chamber is controlled in accordance with a preset program, for example remains essentially constant in step (b) or/and step (d).

Steps (a) and (c) can each be carried out in the same reaction chamber but also in different reaction chambers. The filtration membranes are expediently chosen so that, on the one hand, they are able to retain particulate template materials but, on the other hand, they make rapid removal of the used reaction medium possible. Examples of suitable filter materials are polyamide, cellulose nitrate and cellulose acetate. In order to avoid aggregation or/and blockage of the filter with sensitive template particles, the method is carried out under conditions which suppress adhesion of template particles. Thus, it is possible where appropriate to use for each filtration step membranes which have the same charge as the polyelectrolyte species used in the particular step.

The filtration can be expedited by applying a positive pressure in the reaction chamber or/and a vacuum in the filtrate chamber. With sensitive template particles, in particular biological aggregates, the filtration is essentially carried out without a pressure difference (pressure difference $\leq \pm 0.5$ bar) between reaction chamber and filtrate chamber. In addition, stirring of the reaction chamber is in many cases advantageous, at least during steps (a) or/and (c), in particular continuous stirring throughout the process.

The novel membrane filtration method can be carried out continuously, allows relatively large amounts of coated particles to be produced in a very short time, can be monitored visually and very substantially prevents aggregation of particles. The method can be carried out on an industrial scale and can, by reason of its flexibility, be adapted to different demands of the specific particles and coating systems. On use of soluble template particles it is possible for the cores to be broken down continuously subsequent to the coating.

The invention is explained further by the appended figures and examples.

EXAMPLES

Example 1

Production of Partially Crosslinked Melamine-formaldehyde Template Particles

Monodisperse melamine-formaldehyde polymer particles can be produced by a polycondensation reaction from melamine-formaldehyde precondensates in the range of size up to 15 µm (cf. DD 224 602). The size of the particles can be influenced by the monomer condensation, the pH, the reaction temperature and the addition of surfactant. Methods described in the prior art result in highly crosslinked particles which are insoluble in most organic solvents such as, for example, xylene, toluene and alcohol, and in acids and bases. Partially crosslinked melamine-formaldehyde template particles which can be disaggregated are produced by modifying the method described in the prior art by stopping the polycondensation process at a particular initial stage of the reaction. This results in cores which are soluble in aqueous media. The reaction can be stopped by rapidly lowering the temperature, by changing the pH into the alkaline range and by choosing suitable precondensates, in particular tetramethylolmelamine.

The cores obtained in this way can be disaggregated in aqueous media by addition of acid and/or by particular chemical reactions, in particular sulfonation. The sulfonating agents which can be employed are, in particular, alkali metal sulfites, alkali metal hydrogen sulfites and other water-soluble salts of sulfurous acid. The ability of the cores to be disaggregated can be influenced by the timing of the stoppage of the polycondensation process. The stoppage is carried out 1 min to 3 h after the start of the reaction, depending on the reaction conditions and depending on the required ability of the cores to disaggregate. The rate of disaggregation can further be controlled by the choice of pH, temperature and sulfonation reagent. It is thus possible to obtain cores with a rate of disaggregation of from 0.1 s to 10 h, once again depending on the disaggregation conditions. These melamine-formaldehyde particles capable of disaggregation are referred to herein as partially crosslinked melamine-formaldehyde particles.

Example 2

Production of Empty Polyelectrolyte Shells Using Melamine-formaldehyde Particles as template 2.1

Figure 1:
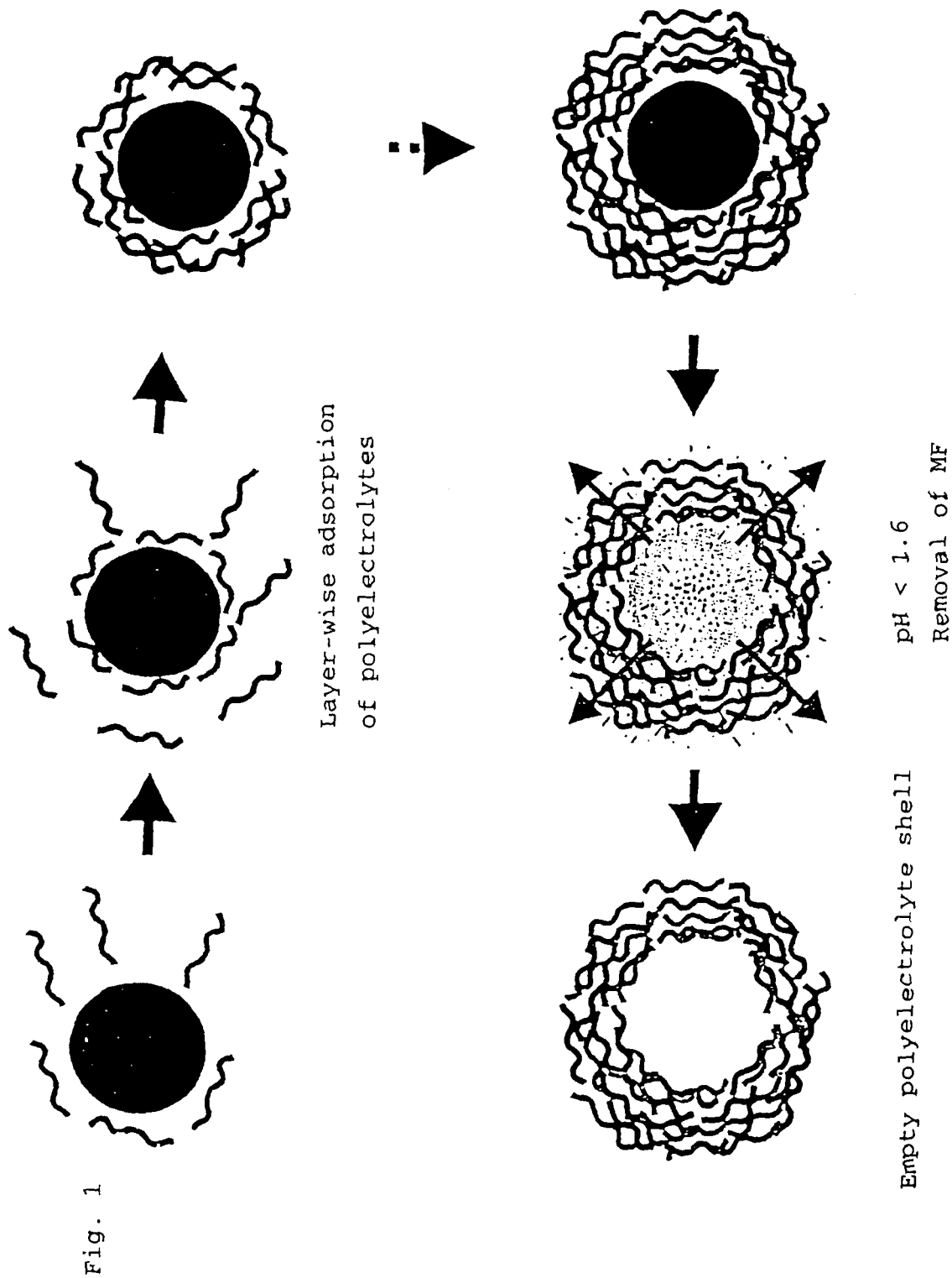
FIG. 1 represents a diagrammatic illustration of a preferred embodiment of the novel method.

Polyelectrolytes are applied stepwise from diluted aqueous solutions to monodisperse, colloidal, partially crosslinked melamine-formaldehyde particles (MF) which have been produced as described in Example 1 and have a diameter of 2.0 or 3.3 µm (cf. FIG. 1). The polyelectrolyte layers are applied by alternate adsorption of oppositely charged polyions, starting with the adsorption of a negatively charged polyanion (for example polystyrene sulfonate, sodium salt; PSS) onto the positively charged MF particles. Typical adsorption conditions were 20 mM polyelectrolyte (stated concentration based on monomer), 0.5M NaCl with particle concentrations of 0.5% by weight. The adsorption time was 20 min. The MF particles had a density of 1.5 g/cm$^3$.

After completion of this adsorption cycle, excess electrolyte was removed by repeated centrifugation/washing cycles.

For this purpose, the coated cores were sedimented at a centrifugation speed of 2000 rpm (by using an Eppendorf rotor). Then three washing steps were carried out with deionized water before adding the next polyelectrolyte in order to ensure complete removal of unadsorbed polyelectrolyte. The required number of polyelectrolyte layers can be applied by repetition of this procedure.

The pH was then reduced to <1.6, by which means the MF cores are disaggregated within a few seconds. The fragments penetrate through the pores in the shell to the outside and can be removed, so that an empty polyelectrolyte shell is obtained. There is no detectable disaggregation of the cores at pH values above 1.8.

2.2

100 μl of a 3% strength dispersion of partially crosslinked melamine-formaldehyde particles with a particle size of 3 μm are mixed with 400 μl of a solution of 20 mM mono PSS in 0.5M NaCl. After an action time of 5 min with gentle shaking, 1 ml of pure water is added. After centrifugation at 2000 rpm, the supernatant is decanted, the sediment is made up with pure water and the centrifugation is repeated. A further decantation and another centrifugation cycle afford purified MF particles covered with a PSS layer. A poly(allylamine hydrochloride) layer (PAH) is subsequently applied in an analogous manner. These cycles are repeated alternately depending on the required number of layers. The centrifugation cycle when the building up of the last layer is complete is followed by addition of 1 ml of a 0.1N hydrochloric acid. Shaking for about 5 min results in a clear solution because the turbidity of the solution caused by the particles has disappeared. This is followed by centrifugation at 10,000 rpm for about 10 min. During this centrifugation a fine sediment which has a slightly milky appearance and contains the formed polyelectrolyte shells separates out. Even gentle shaking after addition of water is sufficient to resuspend the shells. Two further centrifugation steps result in a purified 3% strength dispersion of spherical, monodisperse polyelectrolyte shells in water. A sample of these shells can be examined by scanning electron microscopy, transmission electron microscopy and/or atomic force microscopy.

2.3

1.59 mg of Na polystyrene sulfonate (PSS) are added to a dispersion of partially crosslinked melamine-formaldehyde particles in 0.5M NaCl. The MF dispersion contains a total of $2.2 \times 10^8$ particles. After gentle shaking for 20 minutes, 0.81 mg of polyallylamine hydrochloride is added. After a further 20 min, 1.59 mg of PSS are added with gentle shaking. This procedure is repeated 5× with one PAH addition and one PSS addition each time. This results in melamine-formaldehyde particles covered with 13 alternating layers. The pH is reduced by addition of 10 ml of 1N hydrochloric acid so that the MF cores disaggregate. The polyelectrolyte shells are separated from the supernatant by centrifugation at 15,000 g for 15 min.

Example 3

Figure 2:
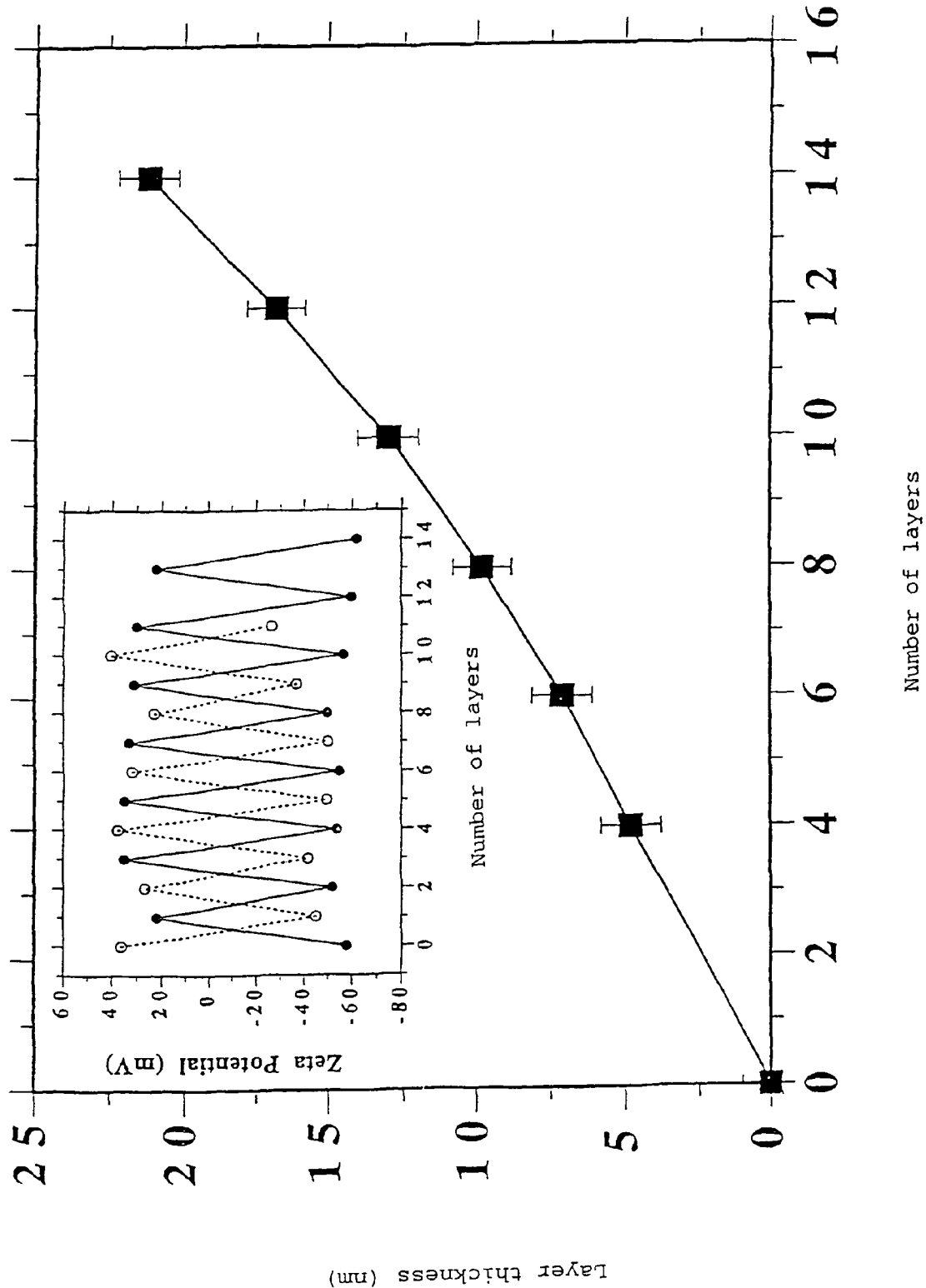
FIG. 2 shows the layer thickness as a function of the number of layers on absorption of poly(allylamine hydrochloride) (PAH) and poly(styrenesulfonate, sodium salt) (PSS) onto negatively charged polystyrene (PS) latex particles.

Characterization of the Polyelectrolyte Shells 3.1 Dependence of the Layer Thickness on the Number of Layers Layers of poly(allylamine hydrochloride) (PAH) and poly(styrene sulfonate, sodium salt) (PSS) were adsorbed alternately onto negatively charged polystyrene (PS) latex particles. The layer thickness was measured by single particle light scattering. The increase in intensity of the scattered light is a measure of the amount adsorbed and was converted into the layer thickness using the refractive index of the polyelectrolyte layers. The insert in FIG. 2 indicates the zeta potential, derived from electrophoretic mobility measurements (Malvern Zetasizer 4), for the adsorption of PAH and PSS onto polystyrene particles (black circles) and for the adsorption of PSS and PAH onto positively charged MF particles (white circles).

The zeta potential is a measure of the effective charge density on the particle surface. As is evident from FIG. 2, the surface potential is reversed with the adsorption of each polyelectrolyte layer onto the polystyrene or MF particles. A reversal of the surface potentoial favors the subsequent adsorption of the oppositely charged polyion.

Investigations by time-of-flight mass spectrometry have shown that on disaggregation of the partially crosslinked MF template particles at a pH <1.6 there is formation of MF oligomers which consist mainly of 5-10 units of tetramethylolmelamine. These MF oligomers have a characteristic cross-sectional dimension of about 1 nm, as determined by molecular dynamic simulations (using the DISCOVERY program). These oligomers are ejected from the core and permeate through polyelectrolyte layers which form the shell, and can finally be removed from the empty shells by centrifugation. This confirms that the shells are readily permeable by molecules with a size in the region of a few nm, in particular $\leq 10$ nm, preferably $\leq 5$ nm.

3.2 Scanning Electron Microscopic Investigations of the Polyelectrolyte Shells

Figure 3:
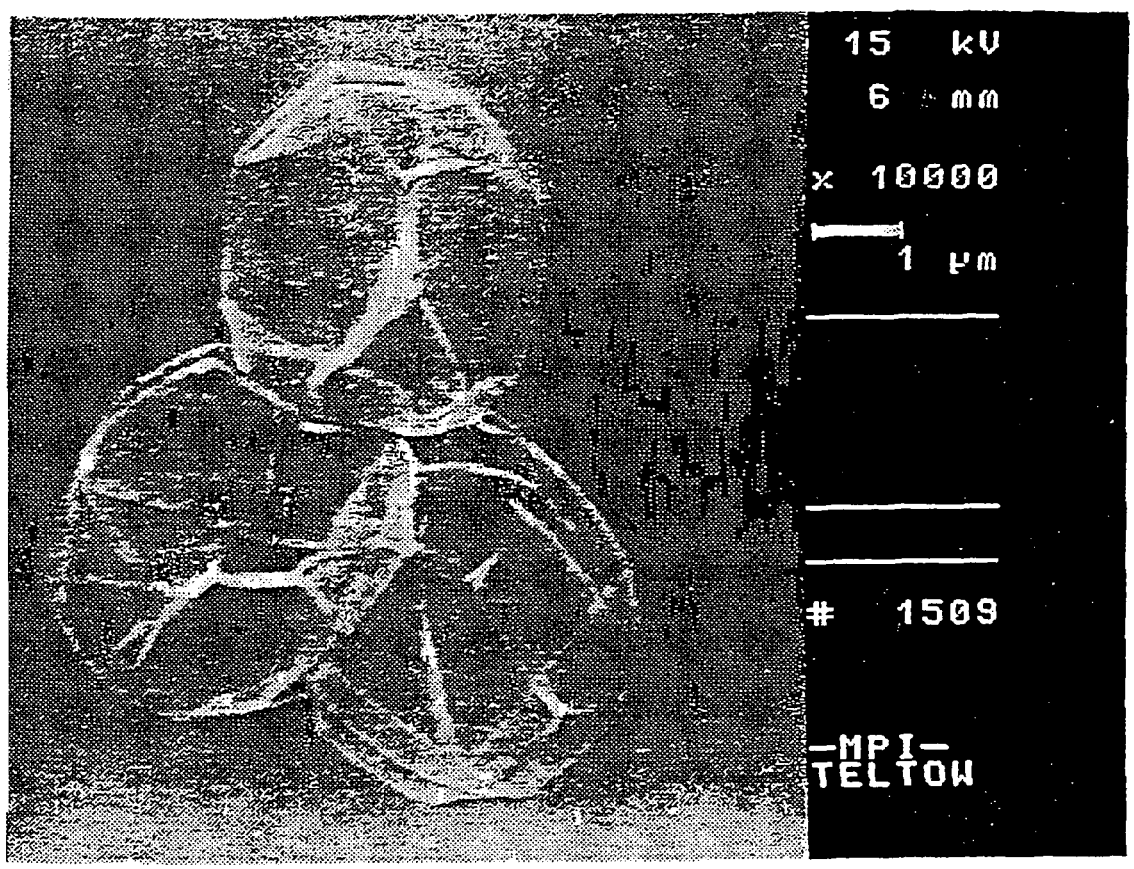
FIG. 3 shows an SEM image (scanning electron microscopy) of a polyelectrolyte shell with nine layers [(PSS/PAH)$_4$/PSS] after disaggregation of the core. The outer layer is PSS.

The polyelectrolyte shells were investigated by scanning electron microscopy (SEM). Firstly an MF core with a diameter of 3.3 μm was coated with 9 polyelectrolyte shells [(PSS/PAH)$_4$/PSS]. The outermost layer is PSS. After disaggregation of the MF core, the resulting capsules were investigated by SEM. As is evident from FIG. 3, the diameters are in the region of 4.0±0.5 μm. The shells are immobilized by a strong electrostatic attraction to the positively charged poly(ethyleneimine)-coated glass surface. In addition, a certain degree of drying of the capsules occurs during the investigation. This leads to the shell becoming wrinkled. However, as is evident from FIG. 3, no holes or traces of fissures are to be found in the shells.

The SEM measurements were carried out using a Zeiss DSM40 instrument which was operated with an accelerating voltage of 15 KeV. The samples were produced by applying a drop of a solution containing the shells to poly(ethyleneimine)-coated glass. After the shells had settled on the glass supports they were thoroughly rinsed with water and cautiously dried under a stream of nitrogen.

3.3 Transmission Electron Microscopy (TEM)

Nine polyelectrolyte [(PSS/PAH)4/PSS] layers were applied to MF template particles with a diameter of 2 μm. The template particles were then disaggregated. The samples were fixed with glutaraldehyde, OsO$_4$ and K$_2$Cr$_2$O$_7$, dehydrated in ethanol/acetone, embedded in an Epon 812/Araldite M resin and polymerized in an oven for two days. Thin sections (80 to 100 nm) were prepared using a Reichert ultratome and stained with uranyl acetate and lead citrate. The measurements were carried out in a JEOL 100 B electron microscope.

Figure 4:
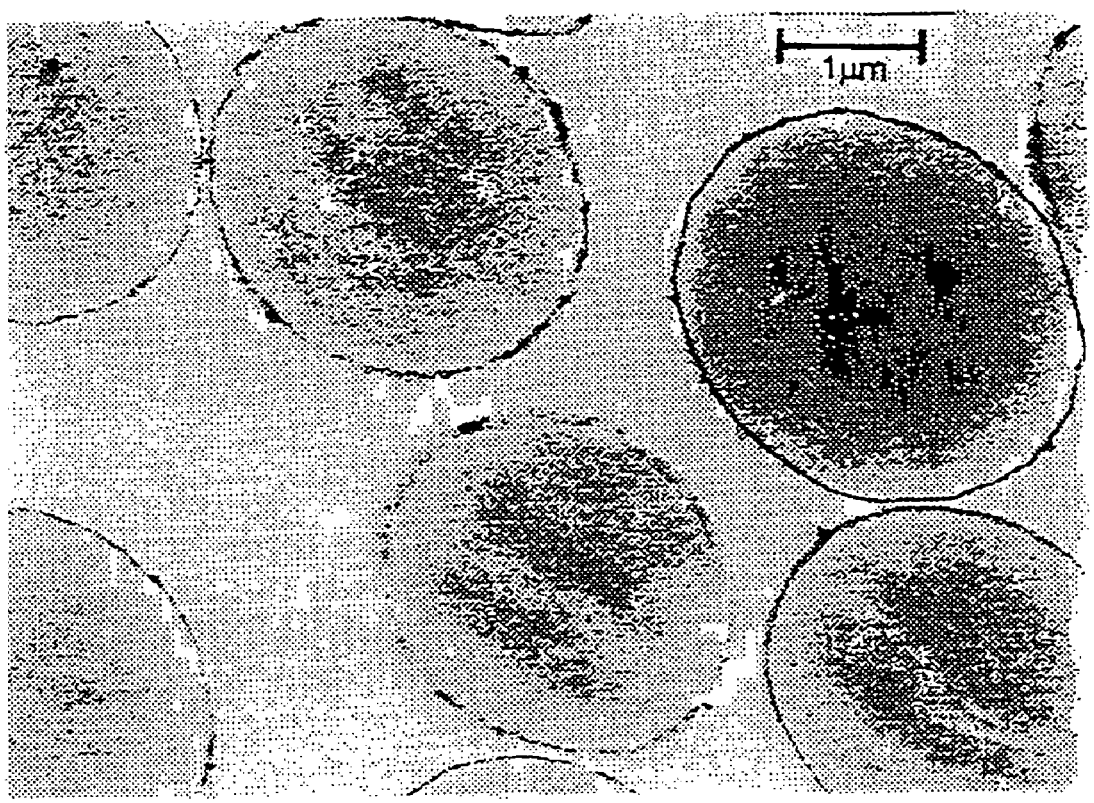
FIG. 4 shows a TEM image (transmission electron microscopy) of a polyelectrolyte shell with nine layers [(PSS/PAH)$_4$/PSS].

As is evident from FIG. 4, the stained polyelectrolyte layer surrounding the more lightly stained interior of the cell can be clearly identified. The homogeneous shape of the shells shows that the produced capsules retain both the diameter and the spherical shape of the template particles provided the inner aqueous solution is not removed. It is further evident that the thickness of the polyelectrolyte shell consisting of nine layers is of the order of 20 nm. This value agrees with the data shown in FIG. 2 for polyelectrolyte-coated polystyrene particles. It can be concluded from this that the nature of the template particles has a negligible effect on the thickness of the polyelectrolyte layers. It is also evident from the TEM image that the polyelectrolyte shells have neither fissures nor holes.

3.4 Atomic Force Microscopic (AFM) Investigations

Figure 5:
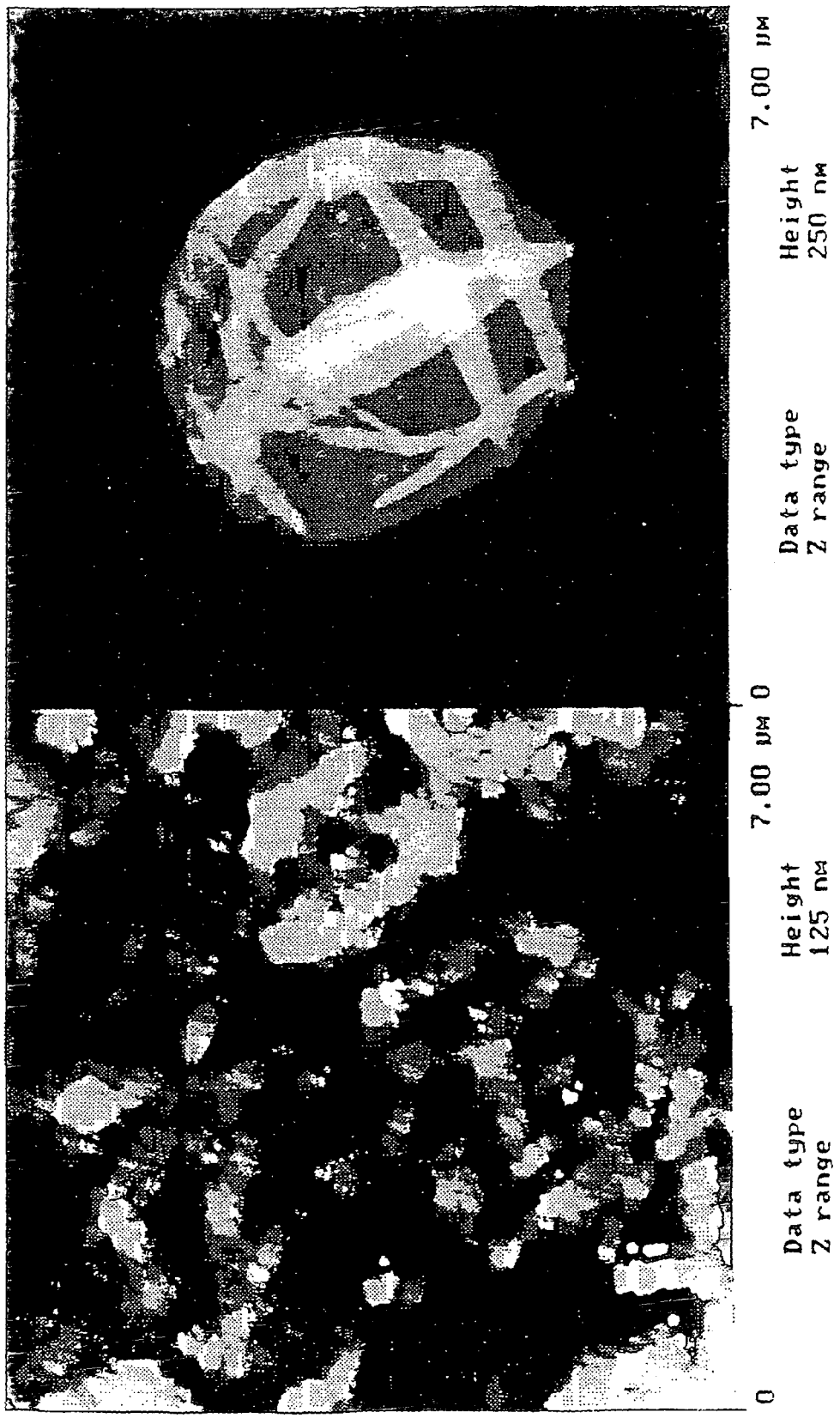
FIG. 5 shows atomic force micrographs of PSS/PAH polyelectrolyte shells. The number of polyelectrolyte shells is 3 [PSS/PAH/PSS] in FIG. 5(A) and 9 [(PSS/PAH)$_4$/PSS] in FIG. 5(B).

PSS/PAH polyelectrolyte shells were produced as described above using MF template particles with a diameter of 3.3 µm. The number of polyelectrolyte layers was 3 [PSS/PAH/PSS] (FIG. 5(A)) or 9 [(PSS/PAH)$_4$/PSS] (FIG. 5(B)). These capsules were investigated by AFM in the tapping mode (TM). FIG. 5 shows that the three-dimensional polyelectrolyte shells are continuous films having wrinkles which result from evaporation of the aqueous interior. As can be seen, the height of the capsules increases as the number of layers increases. The maximum height of the dried shells in Figure A is of the order of 50 nm and in FIG. 5(B) is of the order of 100 nm.

Example 4

Production of Polyelectrolyte Shells Immobilized on a Support

A carefully cleaned glass support is immersed in an aqueous solution of 0.5 mg/ml of poly-ethyleneimine for 5 min. The glass support is then blown dry under a stream of nitrogen. 100 µl of a 3% strength dispersion of partially crosslinked melamine-formaldehyde particles with a particle size of 1 µm diameter are mixed with 400 µl of a 20 mM mono Na poly(styrenesulfonate) solution in NaCl. After shaking gently for 5 min, 1 ml of pure water is added. After centrifugation at 2000 rpm, the supernatant is decanted, the sediment is made up with pure water, and the centrifugation is repeated. A further decantation and another centrifugation cycle result in MF particles covered with a PSS layer. Then 400 µl of a 20 mono mM polydiallyldimethylammonium chloride solution in 0.5M NaCl are added to the particles and incubated for 20 min. This procedure is repeated a second time. The particles are then again coated with PSS as described above and centrifuged three times. The sediment is redispersed in 0.5 ml of pure water and applied to the glass support. After 5 min, the glass support is immersed in a 0.1N hydrochloric acid solution for 5 min. The glass plate is then immersed three times in pure water, without drying in between, for 5 min each time. The glass plate is then dried under a gentle stream of nitrogen. The result obtained is tightly packed polyelectrolyte shells immobilized on a polyethyleneimine-coated glass support and consisting of 5 layers.

Example 5

Entrapment of Active Ingredients in Polyelectrolyte Shells

100 µl of a 2% strength dispersion of partially crosslinked melamine-formaldehyde particles with a particle size of 0.9 µm diameter are mixed with 400 µl of a 0.5M NaCl solution, pH 6, containing 0.5 mg/ml polylactic acid. After shaking gently for 5 min, 1 ml of water is added. After centrifugation at 2000 rpm, rotor radius 5 cm, the supernatant is decanted, water is replenished and the centrifugation is repeated. A further decantation and another centrifugation cycle result in melamine particles covered with a polylactic acid layer. These are mixed with 0.4 ml of a 1 mg/ml lysozyme solution at pH 6.0 and incubated for 20 min, shaking gently. This is followed by washing three times in water. Another polylactic acid layer is applied as described above at pH 6. A poly (allylamine hydrochloride) layer (PAH) is then applied, followed by further layers in the sequence PSS/PAH/PSS.

The particles are then transferred into a 0.1N hydrochloric acid solution. After a few seconds, lysozyme-filled polyelectrolyte shells are formed by disaggregation of the cores and the two polylactic acid layers. These shells are centrifuged in pure water at 15,000 g twice. The supernatant is discarded each time. The resulting sediment comprises concentrated capsules filled with lysozyme, a protein, and having a polyelectrolyte shell of 4 layers. Other biological macromolecules can be encapsulated in a similar way.

Example 6

Production of Empty Polyelectrolyte Shells Using Biological Particles as Template Bovine or human erythrocytes are fixed with glutaraldehyde in a concentration of 2%. After an action time of 60 min at 20° C., the solution is removed by centrifugation and the erythrocytes are washed four times in double-distilled water. The fixed erythrocytes are then made up with unbuffered 154 mM NaCl solution.

For the coating, 4 ml of solution with a concentration of 0.5 g/dl PAH and 0.5M NaCl are made up with an erythrocyte concentration of about 2.5% (v/v). After an action of 10 min at 20° C., the erythrocytes are removed by centrifugation and washed twice in a 154 mM NaCl solution. Then 4 ml of solution with a concentration of 0.5 g/dl PSS and 0.5M NaCl and an erythrocyte concentration of about 2.5% (v/v) are made up. After an action time of 10 min at 20° C., the erythrocytes are removed by centrifugation and washed twice in a 154 mM NaCl solution. The application of PAH and PSS layers can be repeated as often as desired.

The template can be disaggregated in a 1.2% strength NaOCl solution. Commercially available deproteinizing agents (Medical Instruments) or drain cleaners (for example Chlorix) are equally suitable. The action time is about 20 min at 20° C. and can be checked visually by the disappearance of the turbidity of the solution. The remaining polymer shells are then washed in NaCl solution.

It is also possible to coat E. coli or yeast cells in an analogous way. Unfixed cells can also be coated.

Example 7

Deposition of Lipid Layers onto Poly-electrolyte Shells

Two different methods were used to deposit lipid layers on polyelectrolyte shells.

7.1

200 µl of a suspension of polyelectrolyte shells are resuspended by repeated washing in methanol. After the third wash, 500 µl of a lipid solution of, for example, 1 mg/ml dipalmitoylphosphatidic acid (DPPA) or dipalmitoylphospatidylcholine (DPPC) in methanol are added to the sediment in place of pure methanol. The shells are resuspended in this methanolic lipid solution, and the suspension is kept at a temperature of 90° C. in a water bath. The evaporating methanol is replaced by dropwise addition of water in 20 µl portions. Replacement of 700 µl of methanol by water takes about 30 min.

After completion of the evaporation, the suspension of shells is washed three times with water and repeatedly centrifuged. The lipid-coated shells can be sedimented by centrifugation at 25,000 rpm for 20 min.

7.2

Dispersions of DPPA or 90% DPPC and 10% DPPA with a concentration of 1 mg of lipid/ml in water are prepared by ultrasound treatment. 500 µl of the resulting dispersion of lipid vesicles are added to 200 µl of a concentrated suspension of shells. After 30 min, the samples are centrifuged at 25,000 rpm for 20 min. The supernatant is discarded and replaced by water. This procedure is repeated three times. The result is a concentrated suspension of lipid-coated shells.

Example 8

Entrapment of Organic Solvents in Polyelectrolyte Shells

An aqueous suspension of polyelectrolyte shells is centrifuged at 3000 rpm for 5 min. Removal of the supernatant is followed by addition of methanol. The shells are resuspended and centrifuged at 4000 rpm for 10 min. The supernatant is again removed, methanol is added and the sample is centrifuged under the same conditions as before. This procedure is repeated three times. After the last centrifugation with methanol, the supernatant is replaced by hexanol. The shells are resuspended and centrifuged at 5000 rpm for 10 min. This procedure is repeated three times again.

A similar procedure is used to entrap octanol, octane or decane in the shells, using as starting material the shells present in a hexanol solution. The centrifugation speed is increased to 7000 rpm (10 min) for octanol and octane and to 7500 rpm (10 min) for decane.

The resulting sediment is finally resuspended in water. The shells remain in the aqueous phase, while the traces of solvent still present in the sediment form a second organic phase between the shells. By using fluorescent markers for the organic and the aqueous phase it is possible to show by confocal microscopy that the shells are filled with organic solvent.

The described procedure makes it possible to produce a very stable emulsion of nonpolar liquids in water. The monodispersity of the original shells results in the emulsion produced likewise being monodisperse. Another advantage is that even the shape of the individual droplets can be controlled—depending on the template used. This makes it possible to produce emulsions with surface area:volume ratios different from those of a sphere.

Example 9

Precipitation and Crystallization in Polyelectrolyte Shells

The empty polyelectrolyte shells can also be used for controlled precipitation or crystallization of organic or inorganic materials. For this purpose, polyelectrolyte shells are incubated in a 30 mM 6-carboxyfluorescein (6-CF) solution at pH 7. The pH of the solution is then rapidly changed to a value of 3.5, at which 6-CF is substantially insoluble. Incubation for 1 to 12 h results in a mixture of completely 6-CF-filled and empty shells. It was possible in further experiments to precipitate rhodamine B in polyelectrolyte shells by increasing the pH.

The precipitation of active ingredients can also be induced by other measures, for example solvent replacement, salt precipitation etc. These results show that the polyelectrolyte shells can be used as templates for crystallization or precipitation processes, making it possible to control the size and shape of colloidal particles resulting from the reaction.

Example 10

Polymerization in Polyelectrolyte Shells

A 3% solution of diallyldimethylammonium chloride (DADMAC) is mixed in a 2% strength suspension of polyelectrolyte shells with the polymerization initiator sodium peroxodisulfate (30 mg/100 ml) and polymerized at 70° C. for 9.5 h. The polymer PDADMAC synthesized in the volume phase is removed by centrifugation. The presence of polymer adsorbed to the negatively charged capsule walls and polymer present inside the capsule can be detected by treatment with 100 mM 6-CF, which binds to the amino groups of PDADMAC.

Polyelectrolyte shells consisting of 9 layers ([PSS/PAH]$_4$PSS) are deposited on human erythrocytes, and the template particles are removed. A further PAH layer is then applied. The capsules are used for free-radical polymerization of acrylic acid to polyacrylic acid. For this purpose, a 3% strength monomer solution is mixed in a 2% strength capsule suspension with the initiator sodium peroxodisulfate (30 mg/100 ml) and polymerized at 70° C. for 9.5 h. The polyacrylic acid synthesized in the volume phase is removed by centrifugation. The presence of polyacrylic acid adsorbed onto the negatively charged capsule walls, but also inside the capsules, can be detected after addition of 100 mM rhodamine B, which binds selectively to anionic groups. The adsorption of acrylic acid to capsule walls can be prevented by using capsules with an external negative charge.

Example 11

Colloidal Stabilization of Poly-electrolyte Shells Filled with Organic Solvents

Polyelectrolyte shells in aqueous solution are loaded with DPPA (with addition of 5% labeled DPPC). The aqueous dispersion is mixed with pentanol, octanol or decane. The samples are centrifuged at 17,000 rpm for 2 min. The mixture separates into two phases, with the shells being located at the layer between the aqueous and the organic phase. The aqueous phase is extracted and the sample is washed three times with the organic solvent.

It can be demonstrated by confocal microscopy that the lipids remain on the shells even after contact with the organic solvent and that an aqueous phase is encapsulated inside the shell. For this purpose, before application of the lipid layer, the capsules are incubated in a 0.1 mM 6-CF solution for 1 h and, after application of the lipids, the sample is washed four times with water to remove excess lipids and 6-CF. A confocal image recorded 12 h after the preparation shows that the aqueous 6-CF solution is still encapsulated inside the shells. The organic solvent shows no fluorescence.

These results show that the polyelectrolyte shells can be used for encapsulating organic solvents in water and, conversely, also for encapsulating an aqueous phase in an organic medium. It is thus possible to produce stable oil-in-water and water-in-oil emulsions without using surface-active agents.

Example 12

Production of Polyelectrolyte Shells by Membrane Filtration 12.1 Materials

The template particles used were charged polystyrene latex particles with a diameter of 640 nm, which were produced by the method of Furosawa et al. (Colloid-Z. Z. Polym. 250 (1972), 908), partially crosslinked melamine-formaldehyde particles with diameters of 3.7 µm and 5 µm, and glutaraldehyde-fixed human erythrocytes. The coating substances used are sodium poly(styrenesulfonate) PSS (MW 70,000), poly (allylamine hydrochloride) PAH (MW 8000 to 11,000), poly (diallyldimethylammonium chloride) PADMAC (MW 100, 000), chitosan (MW 200,000 to 300,000), chitosan sulfate (MW 200,000 to 300,000) and magnetite particles. For this purpose, aqueous solutions of 1 or 2 mg/ml PSS, PAH or PDADMAC in 0.5M NaCl are prepared. Chitosan sulfate is prepared as solution with a concentration of 1 mg/ml in 0.5M NaCl. Chitosan is dissolved at a concentration of 1 mg/ml in 0.5M NaCl with addition of 0.3% (v/v) acetic acid.

An SM 16692 vacuum pump (Sartorius AG, Gottingen, Germany) is used for the membrane filtration, with which it is possible to produce a vacuum of about 100 mbar and a positive pressure of up to 3 bar. An SM 16510 polycarbonate filtration unit (Sartorius) is used for the vacuum filtration, and an SM 16526 unit (Sartorius) is used for the pressure filtration.

Membrane filters with a diameter of 47 mm of the following types are used: Sartolon polyamide SM 25007-047 N (0.2 µm), Sartolon polyamide SM 25006-047 N (0.45 µm), cellulose acetate SM 11104-047 N (0.8 µm) and cellulose nitrate SM 11306-100 N (0.45 m).

12.2 Methods

Polystyrene and melamine-formaldehyde latex suspensions are employed at a concentration of from 1 to 30% (v/v). The concentration of the erythrocyte suspension should not exceed about 10% (v/v). The volume of the particle suspensions used in the first adsorption step is between 10 ml and 50 ml. The adsorption time is always 5 min. The particles are then washed with water.

The membrane filtration can be carried out as vacuum filtration, pressure filtration and filtration without change of pressure. It is preferable during the polyelectrolyte adsorption to apply a slight reduction in pressure in the incubation chamber relative to the lower filtrate chamber in order to avoid loss of the incubation medium and the polyelectrolyte during the adsorption.

One aspect in the selection of the membrane filter is the sign of the charge on the polyelectrolyte to be adsorbed. Polyamide filters, for example, are suitable in the case of polycations (PAH, chitosan). Cellulose acetate or celluose nitrate filters can be used in the case of polyanions. It is possible in this way to minimize blockage of the filter by polyelectrolyte adsorption.

It is expedient to carry out the filtration under conditions with which formation or compaction of the filter cake is avoided or restricted. Adhesion of PS and MF latex particles with an outer layer of PSS or PAH to the filter surfaces, as well as the tendency to aggregation or/and flocculation thereof, is slight. Filtration is therefore possible up to high particle concentrations (20%) without interruption or replacement of the filtered suspension medium by the washing medium. In the case of erythrocytes, care is needed during the deposition of the first four or five layers in order to prevent aggregation. The concentration of the suspension should therefore not exceed about 5 to 10% (v/v), and the formation of a filter cake should be avoided as far as possible. After completion of the initial adsorption cycles there is a decrease in the tendency to aggregation and in the tendency to adhere to the filter. Any flocculation occurring during the addition of a polyelectrolyte can be redissolved or broken up during the course of the process by adding an oppositely charged poly-electrolyte, for example the following polyelectrolyte, without damaging the product.

Similar results are obtained with the chitosan/chitosan sulfate system. Substantially complete suppression of aggregation can be achieved by stirring.

12.3 Results

Figure 6:
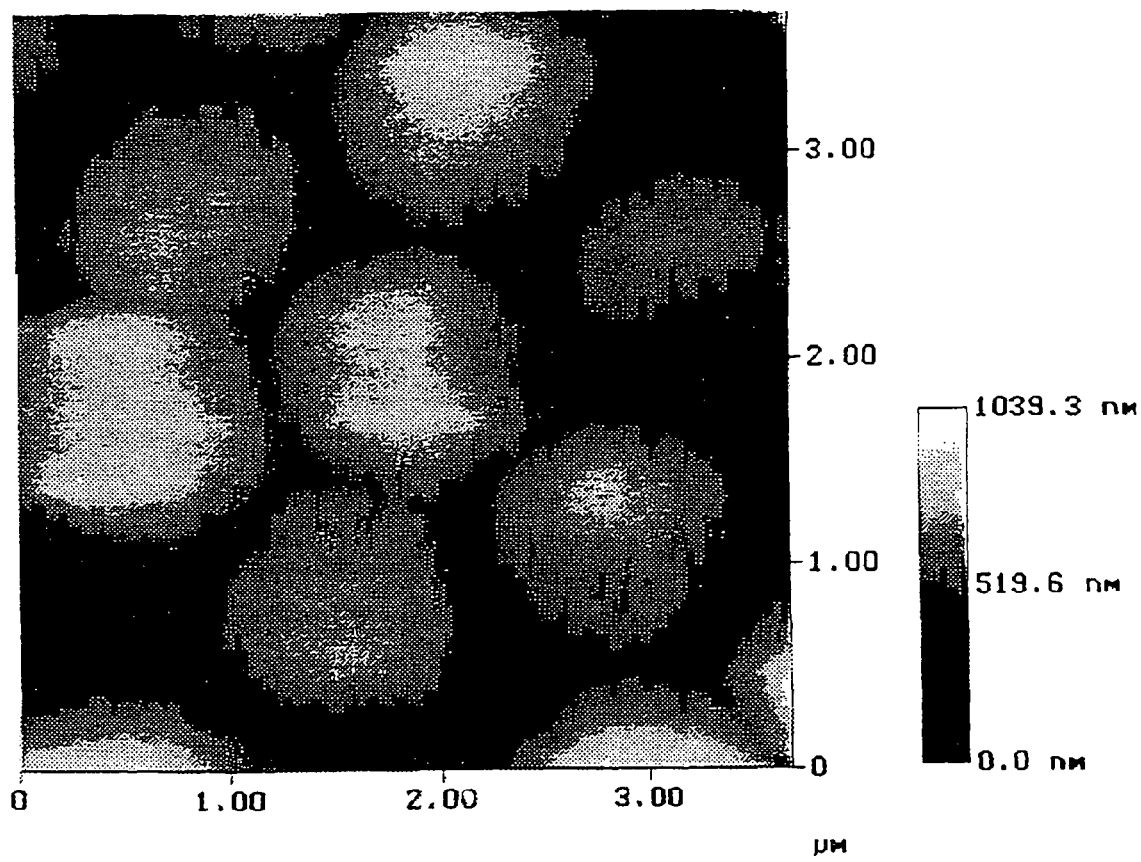
FIG. 6 shows an AFM image of PS latex particles with a diameter of 1.28 µm and a polyelectrolyte shell with six layers (PAH/PSS)$_3$. The outer layer is PSS.

FIG. 6 shows an AFM image of PS latex surfaces after application of 3 PAH/PSS pairs of layers. The surfaces are smooth and no polyelectrolyte aggregates are evident. These particles were produced by vacuum membrane filtration with a suction pressure of about 100 mbar and with use of 450 nm cellulose nitrate membrane filters. It is likewise possible to use polyamide filters or alternately negatively charged celluose acetate and positively charged polyamide filters.

Figure 7:
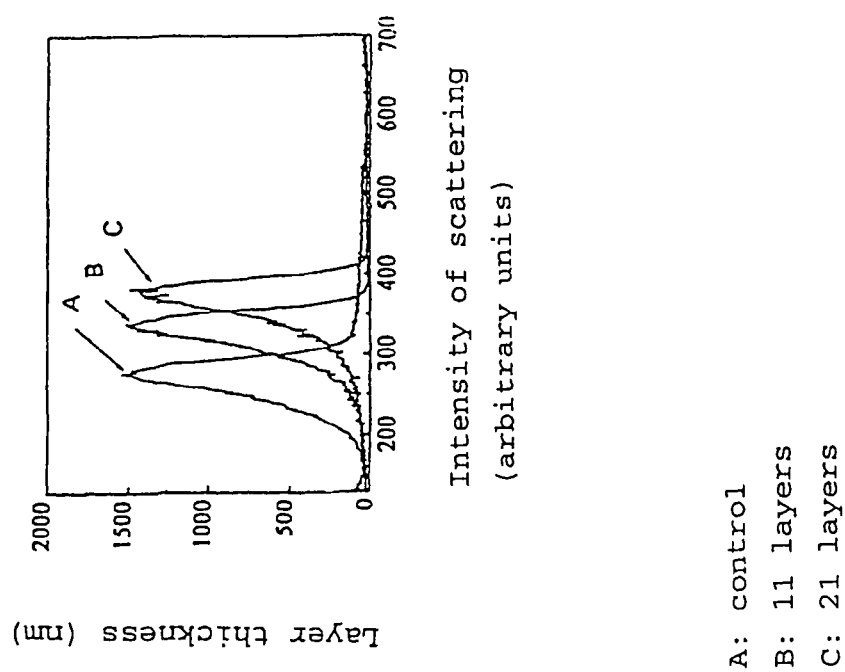
FIG. 7 shows normalized light-scattering intensity distributions of PAH/PSS-coated PS latex particles. Particles with 11 and 21 layers are compared with the uncoated particles.

In FIG. 7 there is determination of the growth of the thickness of the shells on the surface of 640 nm PSS latex particles by single particle light scattering by the method described by Lichtenfeld et al. (Colloid Surfaces A 104 (1995), 313). The scattered light intensity increases with the particle size. The results for particles with 11 and 21 PAH/PSS layers are shown, compared with uncoated particles.

Figure 8:
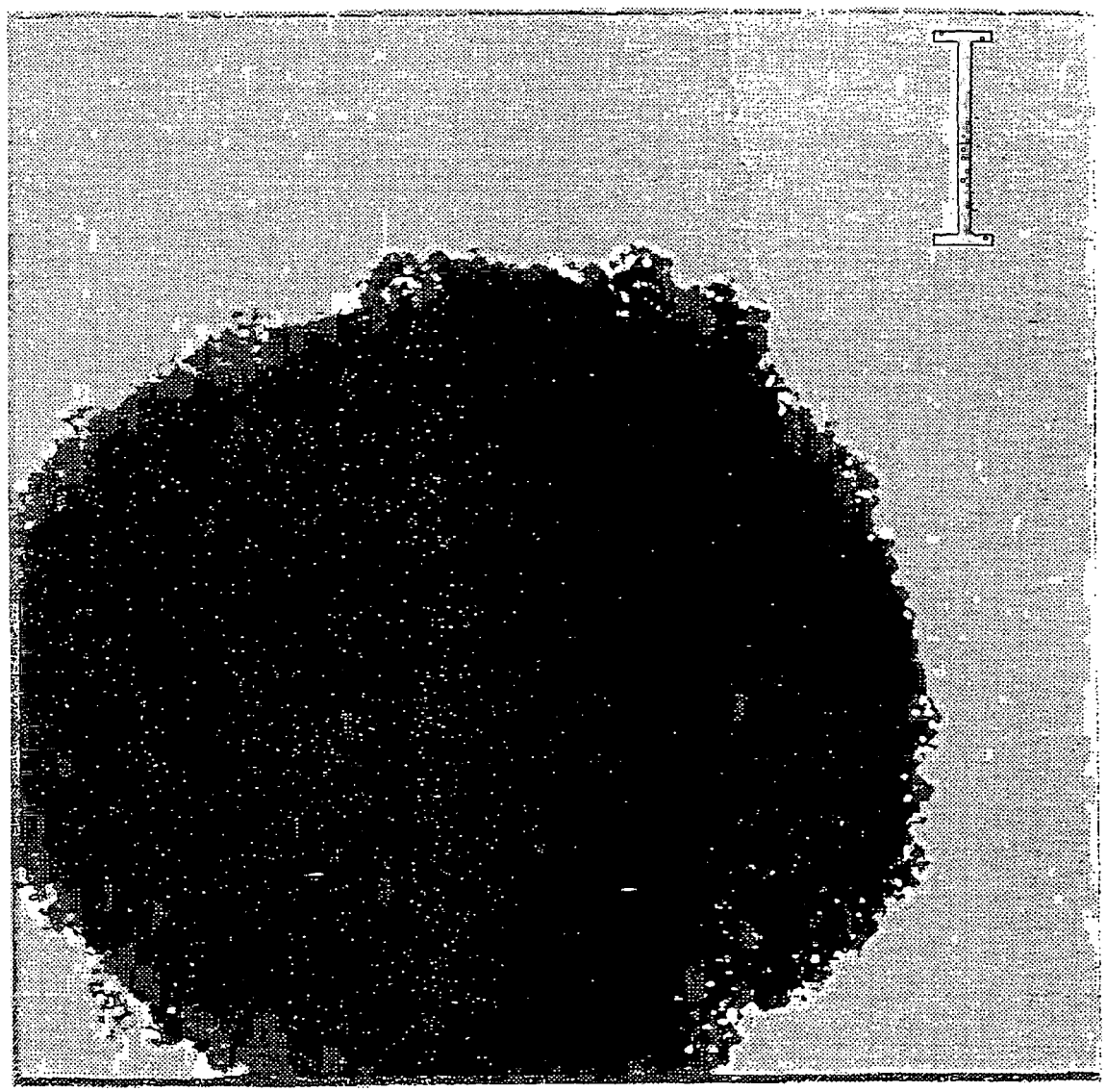
FIG. 8 shows a TEM image of a PS latex particle coated with four PAH/PSS layers and then three pairs of layers each consisting of one magnetite layer and one PSS layer. The scale corresponds to 200 nm.

The TEM image of a with a mixed layers of polyelectrolyte and magnetite particles which were produced by precipitation of iron(II) and iron(III) salts in ammonium hydroxide solution and stabilization by HCl (Massart and Cabuil, J. D. Chemie Physique 84 (1987), 967) is shown in FIG. 8. Firstly two PAH/PSS bilayers are adsorbed. Then three magnetite/PSS bilayers are adsorbed. The filtrate solution was in each case colorless and clear. This denotes complete adsorption of the magnetite. Magnetite aggregates formed on the surface are clearly evident.

Figure 9:
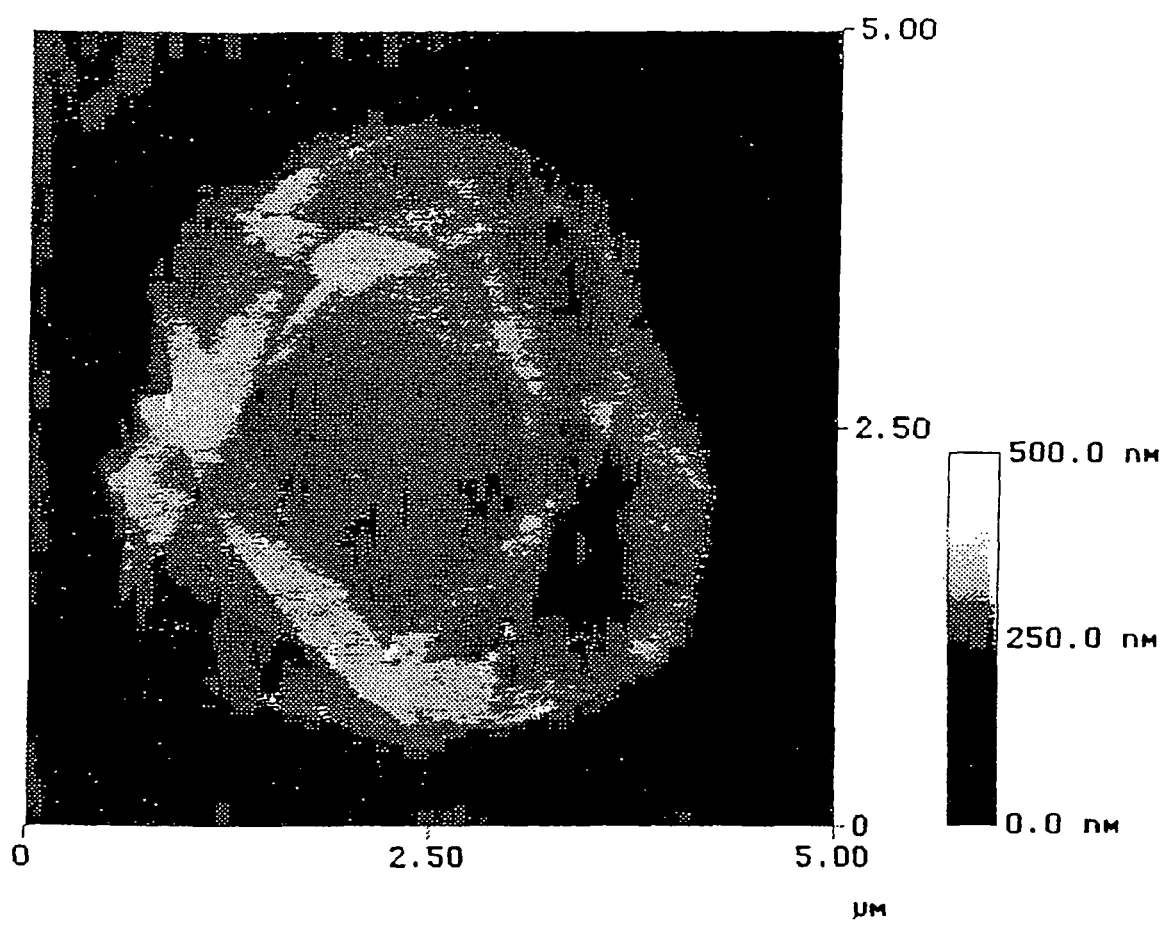
FIG. 9 shows an AFM image of a polyelectrolyte shell produced by coating a 3.7 µm MF latex particle with 10 PSS/PAH layers and then disaggregating the template particle.

On use of MF particles capable of disaggregation as template the results of the membrane filtration are likewise good. Microcapsules with 10 PAH/PSS layers of 3.7 µm MF particles are shown in the AFM image in FIG. 9. The template particles were disaggregated in citrate buffer pH 1.4. The morphology of the flat shell is clearly evident.

Figure 10:
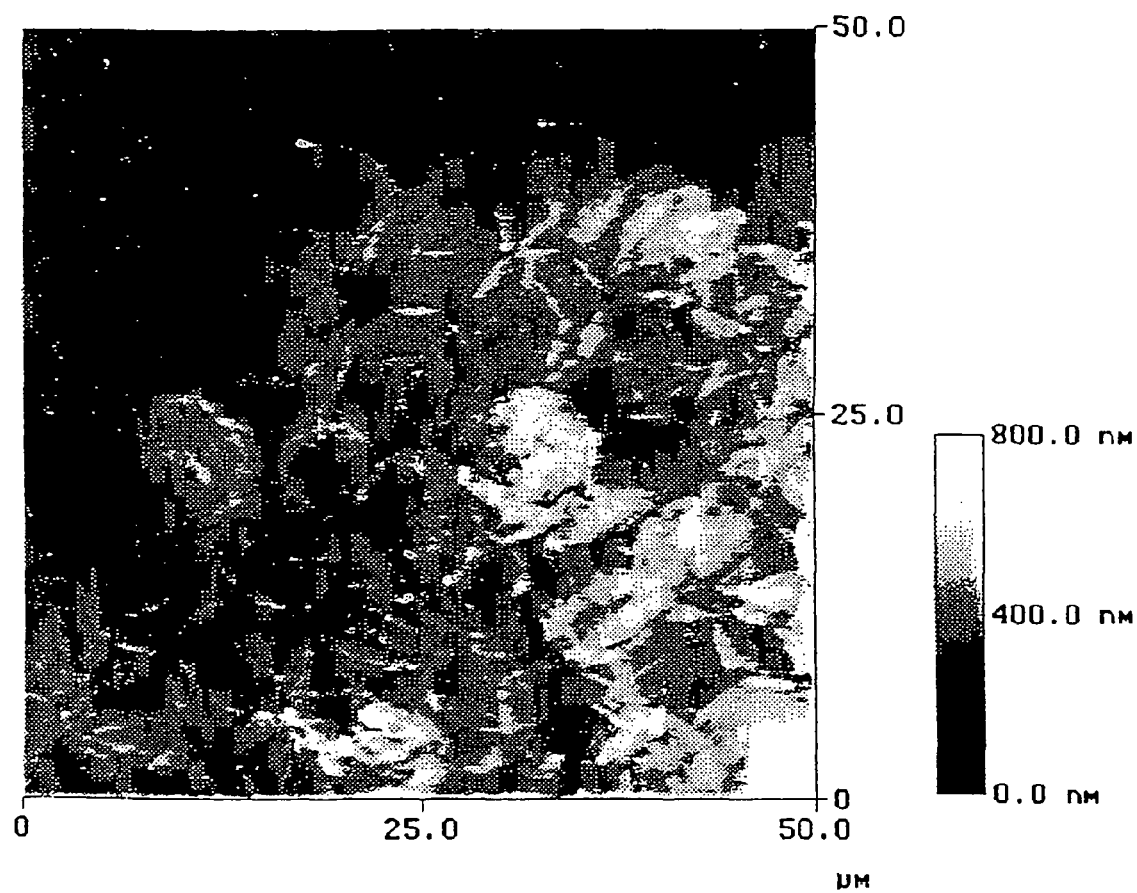
FIG. 10 shows an AFM image of polyelectrolyte shells obtained by coating glutaraldehyde-fixed human erythrocytes with ten PSS/PAH layers and then disaggregating the template particle. The scale values on the axes are in µm and the values of the height scale are in nm.

FIG. 10 shows an AFM image of PAH/PSS microcapsules with 10 layers deposited on the surface of glutaraldehyde-fixed human erythrocytes. Despite the negative charge of the cells it is beneficial to start with a PSS adsorption layer. It is possible in this way to reduce the extent of aggregation during the first adsorption steps. The filtration should take place under mild pressure conditions (only slight or no elevation or reduction in pressure) in order to avoid the formation of filter cakes. Similar precautionary measures are necessary on use of PDADMAC as polycation. Excellent results are obtained under conditions without pressure even in such sensitive systems.

Figure 11:
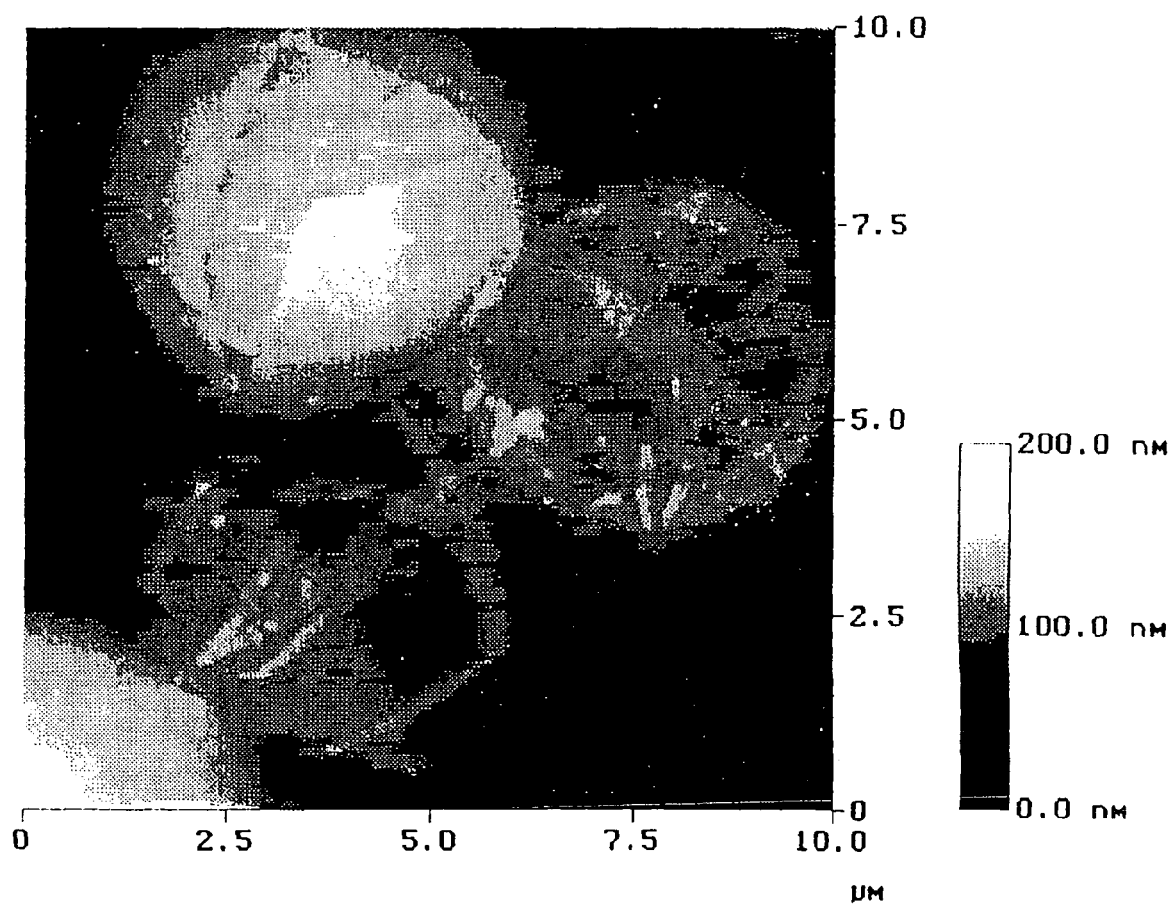
FIG. 11 shows an AFM image of polyelectrolyte shells obtained by coating 3.7 µm MF latex particles with ten chitosan/chitosan sulfate layers and then disaggregating the template particle.
Figure 12:
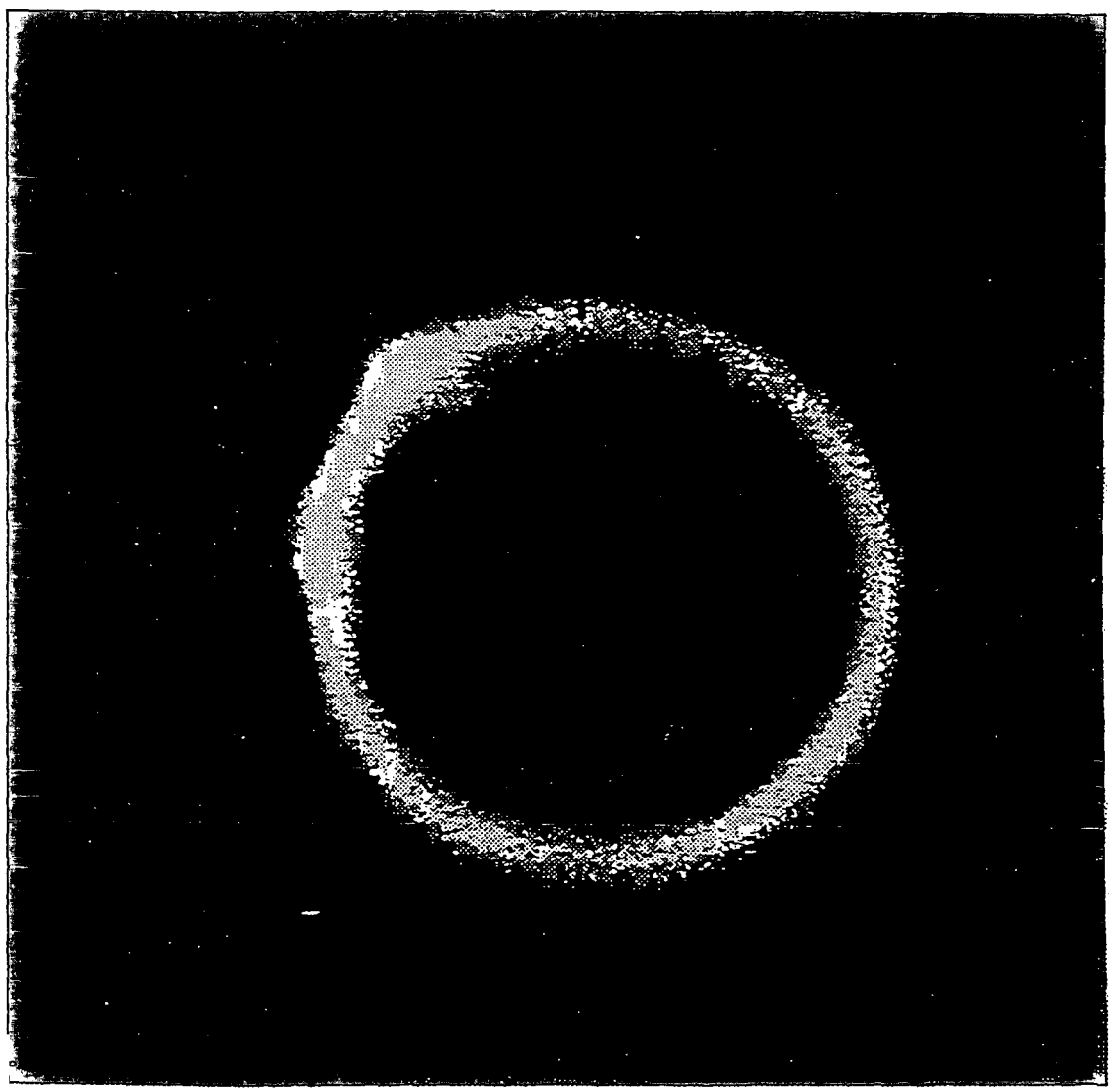
FIG. 12 shows a CLSM image of chitosan/chitosan sulfate microcapsules consisting of eleven layers, where FITC-labeled PAH was used as outermost layer.
Figure 13:
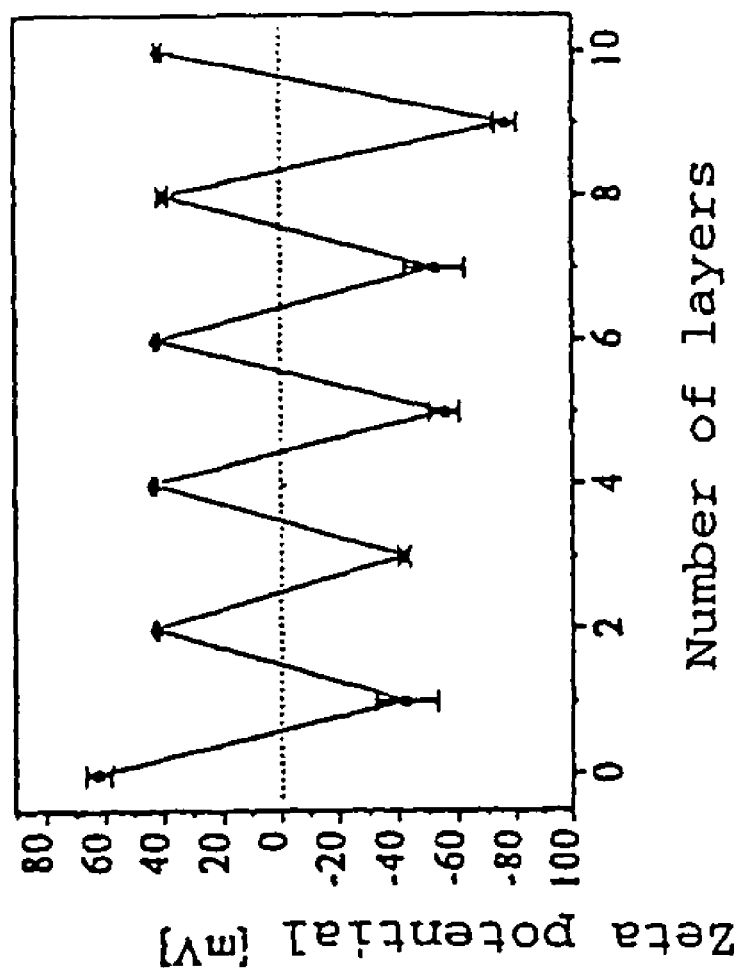
FIG. 13 shows the zeta potential of uncoated and chitosan/chitosan sulfate-coated 3.7 µm MF latex particles.

FIGS. 11 to 13 show results obtained on use of chitosan/chitosan sulfate as polyelectrolyte pair. FIG. 11 is an AFM image of MF particles provided with 10 layers after disaggregation of the core. In order to facilitate investigation of the shell morphology, FITC-labeled PAH was applied as eleventh layer and the shell was investigated by confocal laser scanning microscopy. The result is shown in FIG. 12. FIG. 13 indicates the zeta potentials of layer-wise growing microcapsules. Odd numbers for layers correspond to chitosan sulfate and are characterized by negative zeta potentials. Even-numbered layers correspond to chitosan and show positive zeta potentials.

Example 13

Permeability of Polyelectrolyte Shells

Polyelectrolyte shells were produced by coating 3 µm melamine-formaldehyde particles using sodium poly(styrenesulfonate) with a molecular weight of 70,000 and poly(allylamine hydrochloride) with a molecular weight of 50,000. A PAH labeled with fluorescein isothiocyanate (FITC-PAH) is employed for the confocal fluorescence microscopy (Sukhorukov, Colloids Surfaces A 137 (1998), 253).

Suspensions of melamine-formaldehyde particles with a diameter of 3 µm are coated with 13 PAH and PSS layers. The core is then disaggregated by incubation in 0.1M NaCl for 5 min.

The permeability of the polyelectrolyte microcapsules is investigated by confocal microscopy. For this purpose, initially a solution of PAH-FITC (molecular weight 50,000) is mixed with the shells to give a final concentration of 0.5 mg/ml. The permeability of the shell walls for high molecular weight PAH-FITC is so low that no fluorescence was detectable inside the capsules after incubation for 20 min. In contrast to this, 6-carboxyfluorescein (6-CF) is able easily to penetrate through the walls of the shells.

Figure 14:
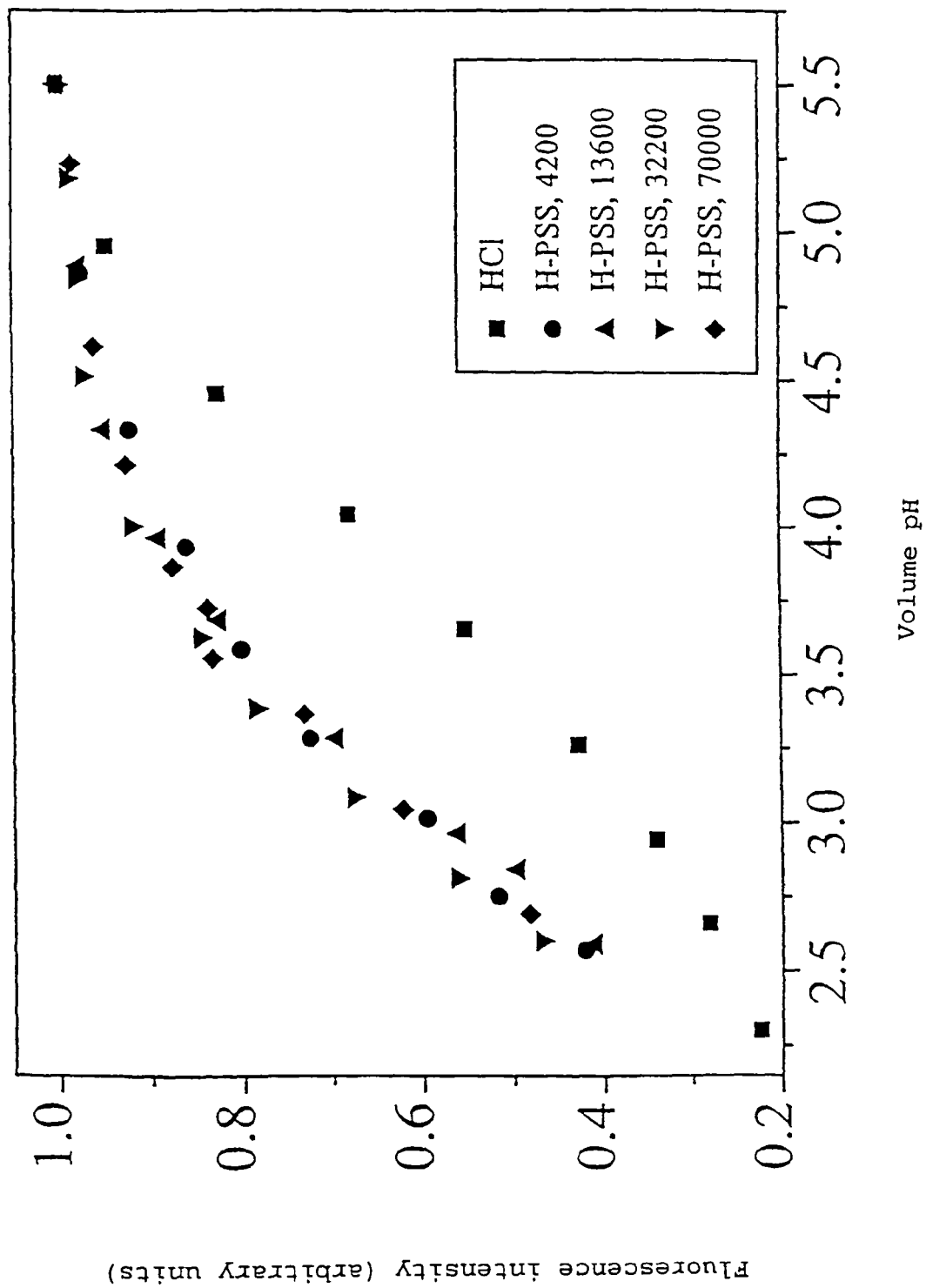
FIG. 14 shows the fluorescence intensity of a suspension, containing 6-CF as fluorescent marker, of polyelectrolyte shells in relation to the pH of the surrounding medium, which was titrated by HCl or H-PSS with the molecular weight stated in each case.

FIG. 14 shows the fluorescence intensity of a suspension of polyelectrolyte capsules containing 6-CF as fluorescent marker in relation to the pH in the surrounding medium titrated with polystyrene sulfonic acid and HCl. The results show that polystyrene sulfonic acid in the respective molecular weights used (70,000-4200) was unable to penetrate through the polyelectrolyte shells.

Figure 15:
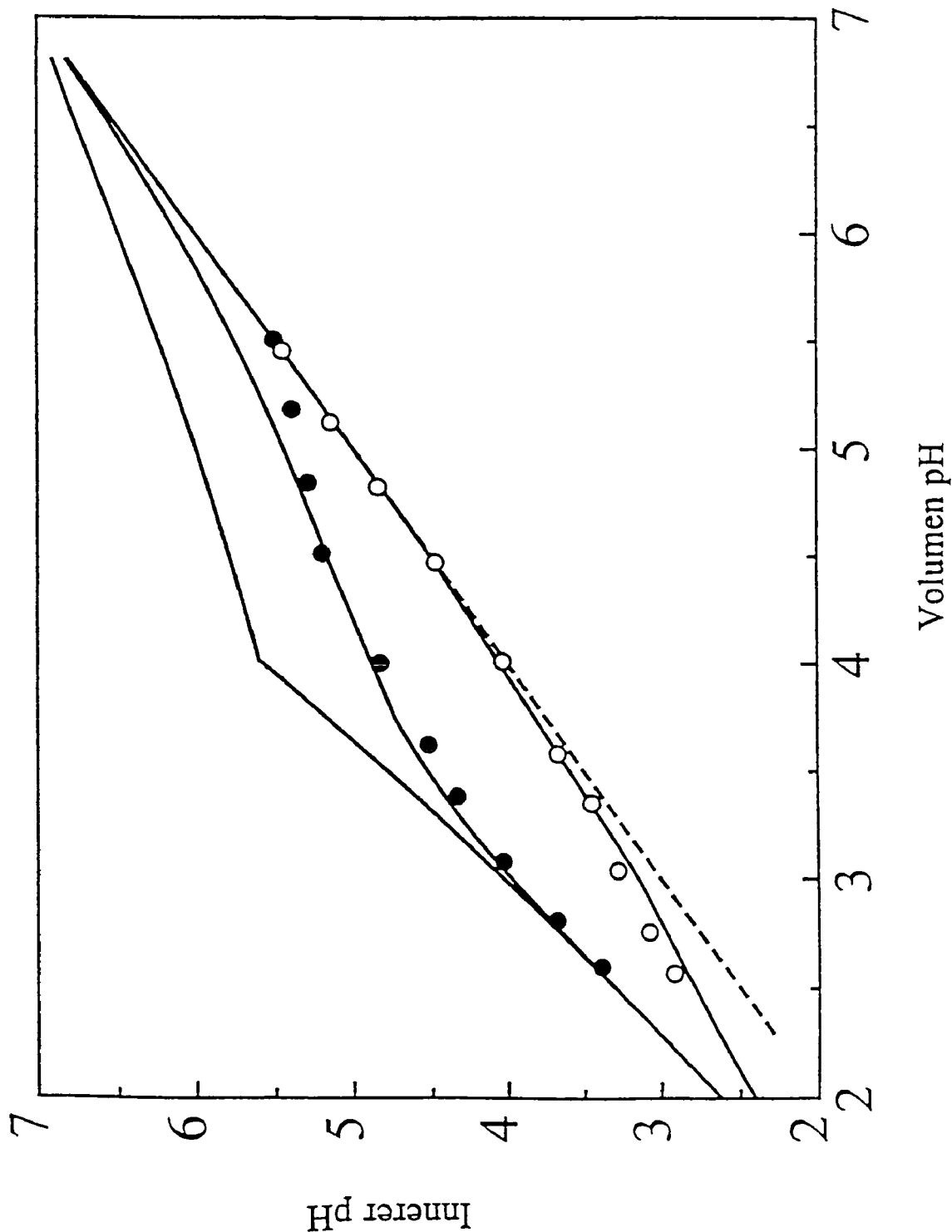
FIG. 15 shows the relation between the pH inside the capsules and the pH of the surrounding medium, titrated with H-PSS (MW 4200) in the absence of salt (black circles) and in the presence of 1 mM NaCl (white circles). The broken line shows the control obtained by titration of the capsule dispersion with HCl.

FIG. 15 shows the pH inside the capsules as a function of the volume pH titrated with H-PSS (molecular weight 4200) in the absence of salt and in the presence of 1 mM NaCl. It is evident that no significant diffusion of PSS polyanions with the respective molecular weights tested into the interior of the capsule takes place at least within one hour. This leads to the development of a pH gradient between the interior of the capsule and the volume. The pH in the interior is about 1 pH more basic than the pH of the volume. This applies in particular when the volume pH is less than 5.5.

The invention claimed is:

1. A method comprising applying a plurality of layers of coating substances to soluble template particles by:
    (a) contacting the soluble template particles with a first coating substance in a fluid reaction medium in a reaction chamber which is limited on at least one side by a filtration membrane, under conditions with which a layer of the first coating substance is formed on the soluble template particles;
    (b) draining at least part of the reaction medium with, where appropriate, excess first coating substance present therein through the filtration membrane into a filtrate chamber;
    (c) contacting the soluble template particles with a second coating substance in a fluid reaction medium in a reaction chamber which is limited on at least one side by a filtration membrane, under conditions with which a layer of the second coating substance is formed on the soluble template particles;
    (d) draining at least part of the reaction medium with, where appropriate, excess second coating substance present therein through the filtration membrane into a filtrate chamber; and
    (e) optionally repeating steps (a) and (b) or steps (c) and (d) a plurality of times,
wherein the first and second coating substances are oppositely charged species or mixtures of polyelectrolyte species, wherein the soluble template particles have a diameter of up to 10 μm, and wherein the method further comprises a disaggregation of the soluble template particles after the completion of step (e).

2. A method according to claim 1, wherein the soluble template particles are selected from biological particles or aggregates.

3. A method according to claim 1, wherein a washing medium is added during or after step (b) or step (d).

4. A method according to claim 3, wherein the addition of the washing medium takes place so that the volume of the medium remains essentially constant in step (b) or step (d).

5. A method according to claim 1, wherein the filtration is carried out essentially without a pressure difference between reaction chamber and filtrate chamber.

6. A method according to claim 1, wherein the reaction chamber is stirred at least during step (a) or (c).

7. A method according to claim 1, wherein the reaction chamber is stirred throughout the process.

* * * * *